(12) United States Patent
Kato et al.

(10) Patent No.: US 6,290,840 B1
(45) Date of Patent: *Sep. 18, 2001

(54) GAS SENSOR AND METHOD FOR CONTROLLING GAS SENSOR

(75) Inventors: Nobuhide Kato, Ama-gun; Yasuhiko Hamada, Nagoya, both of (JP)

(73) Assignee: NGK Insulators, Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/389,245

(22) Filed: Sep. 3, 1999

Related U.S. Application Data

(63) Continuation-in-part of application No. 09/030,900, filed on Feb. 26, 1998.

(30) Foreign Application Priority Data

Mar. 4, 1997 (JP) .................................... 9-49440

(51) Int. Cl.[7] .................... G01N 27/409; G01N 27/41
(52) U.S. Cl. ................... 205/784.5; 205/781; 204/425; 204/426
(58) Field of Search .................... 204/425, 426, 204/428, 427; 205/781, 784.5

(56) References Cited

U.S. PATENT DOCUMENTS

| 4,645,572 | 2/1987 | Nishizawa et al. . |
|---|---|---|
| 5,145,566 | 3/1992 | Logothetis et al. . |
| 5,217,588 | 6/1993 | Wang et al. . |
| 5,763,763 | 6/1998 | Kato et al. . |
| 5,866,799 | * 1/2000 | Kato et al. .................... 73/31.05 |
| 5,879,525 | 3/1999 | Kato . |
| 6,010,615 | * 1/2000 | Kato et al. .................... 205/784.5 |

FOREIGN PATENT DOCUMENTS

| 0 678 740 A1 | 10/1995 | (EP) . |
|---|---|---|
| 0 769 693 A1 | 4/1997 | (EP) . |
| 0 769 694 A1 | 4/1997 | (EP) . |
| 8-271476 | 10/1996 | (JP) . |
| 9-113484 | 5/1997 | (JP) . |

OTHER PUBLICATIONS

Kato et al. Thick Film ZrO2 NOx Sensors, SAE Technical Paper Series, Paper 960334, 1996.

* cited by examiner

Primary Examiner—Robert J. Warden, Sr.
Assistant Examiner—Kaj K. Olsen
(74) Attorney, Agent, or Firm—Parkhurst & Wendel, L.L.P.

(57) ABSTRACT

Disclosed is a method for controlling a gas sensor comprising the steps of pumping-processing oxygen contained in a measurement gas introduced from external space into a first chamber by using a main pumping cell so that a partial pressure of oxygen in the first chamber is controlled to have a predetermined value at which a predetermined gas component as a measurement objective is not decomposable; decomposing the predetermined gas component contained in the measurement gas in a second chamber by the aid of a catalytic action and/or electrolysis by using a detecting pumping cell to pumping-process oxygen produced during the decomposition; and measuring the predetermined gas component contained in the measurement gas on the basis of a pumping current which flows during the pumping process; wherein the oxygen to be pumped out by the detecting pumping cell is pumped out toward an inner pumping electrode which is fixed to have a base electric potential (ground electric potential), of the main pumping cell. Accordingly, it is possible to facilitate miniaturization of a control circuit system of the gas sensor and reduction of the weight thereof.

18 Claims, 11 Drawing Sheets

US 6,290,840 B1

GAS SENSOR AND METHOD FOR CONTROLLING GAS SENSOR

This is a Continuation-in-Part of application Ser. No. 09/030,900 filed Feb. 26, 1998.

BACKGROUND OF THE INVENTION

1. Field of the Invention

The present invention relates to a gas sensor for measuring gas components such as NO, $NO_2$, $SO_2$, $CO_2$, and $H_2O$ contained in, for example, atmospheric air and exhaust gas discharged from vehicles or automobiles. The present invention also relates to a method for controlling the gas sensor.

2. Description of the Related Art

Recently, a gas sensor 10A as shown in FIG. 8 has been known, which is based on the use of an oxygen ion conductor (for example, see Japanese Laid-Open Patent Publication No. 8-271476).

The gas sensor 10A is operated as follows. That is, a measurement gas existing in the external space is introduced into a first hollow space 14 via a first diffusion rate-determining means 12. A first oxygen pumping means 22, which comprises an inner pumping electrode 16, an oxygen ion conductor 18, and an outer pumping electrode 20, is used to pump in or pump out oxygen contained in the measurement gas in the first hollow space 14 to such a degree that the nitrogen oxide as a measurement objective is not decomposed.

Subsequently, the measurement gas in the first hollow space 14 is introduced into a second hollow space 26 via a second diffusion rate-determining means 24. A second oxygen pumping means 36, which is disposed for the second hollow space 26 and which comprises a measurement gas-decomposing electrode 28, an oxygen ion conductor 30, and a reference electrode 34 disposed in a reference air section 32, is used to pump out oxygen produced by decomposition effected by the catalytic action of the measurement gas-decomposing electrode 28 or the electrolysis caused by voltage application. A current value, which is required to pump out oxygen by using the second oxygen pumping means 36, is measured to indirectly measure the nitrogen oxide.

Examples of practical use of the gas sensor 10A include, for example, NOx sensors, $H_2O$ sensors, and $CO_2$ sensors for measuring measurement gases containing those having bound oxygen.

When the conventional gas sensor 10A is applied as an NOx sensor, for example, Rh or Pt is used for the measurement gas-decomposing electrode 28 to catalytically decompose NOx. The oxygen, which is produced during the decomposition, is detected as a pumping current, or the oxygen is detected as a change in voltage.

When the conventional gas sensor 10A is applied as an $H_2O$ sensor or a $CO_2$ sensor, it is difficult to perform catalytic decomposition. Therefore, a voltage, at which each of the gases is decomposable, is applied to the second oxygen pumping means 36. The oxygen, which is produced by electrolysis caused by the voltage application, is detected as a pumping current.

By the way, in the case of the conventional gas sensor 10A described above, a GND line of a DC power source 38 for controlling the first oxygen pumping means 22 cannot be used in common with that of a DC power source 40 for controlling the second oxygen pumping means 36, because of the following reason. That is, the leak current flows from the outer pumping electrode 20 to the measurement gas-decomposing electrode 28, or the leak current flows from the measurement gas-decomposing electrode 28 to the inner pumping electrode 16.

When the current flows through the oxygen ion conductor, the movement of oxygen occurs, in accordance with which the control operation may become unstable, and the pumping current for measurement may be affected. Consequently, it is feared that the measurement cannot be performed.

Therefore, the conventional gas sensor 10A requires two DC power sources which are insulated from each other, for driving the first and second oxygen pumping means 22, 36.

On the other hand, a gas sensor 10B shown in FIG. 9 has been suggested. The gas sensor 10B includes an auxiliary pumping electrode 42 provided in the second hollow space 26 to construct a third oxygen pumping means (i.e., auxiliary pumping means) 46 by the auxiliary pumping electrode 42, oxygen ion conductors (18, 44, 30), and the reference electrode 34. Accordingly, the oxygen, which diffuses to cause invasion in an minute amount from the first hollow space 14, is pumped out again to greatly improve the measurement accuracy (especially, the dependency on oxygen concentration) (Japanese Laid-Open Patent Publication No. 9-113484).

The illustrative suggested gas sensor 10B requires as much as three DC power sources which are insulated and independent from each other, due to the addition of the auxiliary pumping means 46. FIG. 10 shows a control circuit system of the illustrative suggested gas sensor 10B shown in FIG. 9. In this case, the three DC power sources (first DC power source 50A, second DC power source 50B, and third DC power source 50C), which are insulated and independent from each other, are used to control the first, second, and third oxygen pumping means 22, 36, 46.

The first DC power source 50A is used as a power source for a pumping control circuit 52 for controlling the first oxygen pumping means 22. In the pumping control circuit 52, an electromotive force between a measuring electrode 54 and the reference electrode 34 is detected by a first comparator 56. Subsequently, a difference with respect to a target voltage (for example, 300 mV) is determined by a second comparator 58, and the differential voltage is amplified by an amplifier 60. The amplified voltage is applied, as a control voltage $E_0$, between the outer pumping electrode 20 and the inner pumping electrode 16 of the first oxygen pumping means 22. Thus, the first oxygen pumping means 22 is controlled.

The second DC power source 50B is used as a power source for supplying a voltage $E_1$ to the auxiliary pumping means (third oxygen pumping means) 46. Specifically, a constant voltage is obtained by using a Zener diode 62. After that, a voltage $E_1$ to be applied to the auxiliary pumping means 46 is generated by using a voltage-dividing circuit 64, which is applied to the auxiliary pumping means 46.

The third DC power source 50C is used as a power source for supplying a voltage $E_2$ to the second oxygen pumping means 36. The voltage $E_2$ to be supplied to the second oxygen pumping means 36 is generated in accordance with a method similar to that used in the second DC power source 50B, which is supplied to the second oxygen pumping means 36.

As shown in FIG. 11, each of the mutually insulated and independent three DC power sources (hereinafter referred to as "insulated type power source", while a power source, which does not require the insulated and independent arrangement, is hereinafter referred to as "non-insulated type power source") 50A, 50B, 50B is basically constructed by an oscillation circuit 72, an insulated type transformer 74, and a rectifier circuit 76 connected to downstream positions of a battery 70 (for example, 12 V in the case of a car battery). In such an arrangement, the non-insulated type power source can be constructed by using only semiconductor parts such as transistors and operational amplifiers, while the insulated type power source as described above requires the transformer 74. Therefore, it is difficult for the insulated type power source to miniaturize the control circuit system of the gas sensor 10A, 10B and reduce the weight thereof, and an inconvenience is feared in that the production cost becomes expensive.

SUMMARY OF THE INVENTION

The present invention has been made considering the problems as described above, an object of which is to provide a gas sensor and a method for controlling the gas sensor in which it is possible to use a common reference electric potential line (for example, GND line) for a plurality of DC power sources, it is possible to minimize the number of insulated and independent DC power sources (insulated type power sources), and it is possible to miniaturize a control circuit system of the gas sensor and reduce the weight thereof.

According to the present invention, there is provided a gas sensor comprising a main pumping means for pumping-processing oxygen contained in a measurement gas introduced from external space into a processing space formed and comparted by a solid electrolyte contacting with the external space so that a partial pressure of oxygen in the processing space is controlled to have a predetermined value at which a predetermined gas component as a measurement objective is not decomposable; and a detecting pumping means for decomposing the predetermined gas component contained in the measurement gas after being pumping-processed by the main pumping means by the aid of a catalytic action and/or electrolysis, and pumping-processing oxygen produced by the decomposition; wherein the predetermined gas component contained in the measurement gas is measured on the basis of a pumping current which is allowed to flow through the detecting pumping means in accordance with the pumping process effected by the detecting pumping means; and the oxygen to be pumped out by the detecting pumping means is pumped out toward an electrode which is fixed to have a base electric potential, of the main pumping means. However, NO, for example, can be partially decomposed in the main pumping means.

According to the present invention, at first, the oxygen, which is contained in the measurement gas introduced from the external space, is pumping-processed by the main pumping means, and the oxygen is adjusted to have a predetermined concentration. The measurement gas, which has been adjusted for the concentration of oxygen by means of the main pumping means, is introduced into the detecting pumping means in the next step. The detecting pumping means decomposes the predetermined gas component contained in the measurement gas after being pumping-processed by the main pumping means, by means of the catalytic action and/or electrolysis to pumping-process oxygen produced by the decomposition. The predetermined gas component corresponding to the amount of oxygen is measured on the basis of the pumping current generated in the detecting pumping means depending on the amount of oxygen pumping-processed by the detecting pumping means.

Especially, in the present invention, the oxygen to be pumped out by the detecting pumping means during the measurement of the predetermined gas component is pumped out toward the electrode which is fixed to have the base electric potential, of the main pumping means.

As a result, it is unnecessary to provide any DC power source which is insulated and independent from any other DC power source, in order to drive the detecting pumping means. Therefore, the driving voltage can be generated by means of a non-insulated type power source which does not use any insulated type transformer. This consequently facilitates miniaturization of the control circuit system of the gas sensor and reduction of the weight thereof.

It is preferable that the main pumping means comprises the solid electrolyte contacting with the external space, and an inner main pumping electrode and an outer main pumping electrode formed on inner and outer surfaces of the solid electrolyte; the detecting pumping means comprises a solid electrolyte, and an inner detecting pumping electrode and an outer detecting pumping electrode formed in contact with the solid electrolyte; any one of the pumping electrodes of the main pumping means is used in common with the outer detecting pumping electrode of the detecting pumping means; and any one of the pumping electrodes is fixed to have the base electric potential.

In this embodiment, in order to pump out the oxygen by the aid of the detecting pumping means, a detecting voltage is applied between the inner detecting pumping electrode and the outer detecting pumping electrode, wherein a negative voltage is applied with respect to the inner main pumping electrode and the outer main pumping electrode of the main pumping means.

As a result, the reference line (line fixed at the base electric potential) can be commonly used for the power source for the control voltage to be applied between the inner main pumping electrode and the outer main pumping electrode of the main pumping means and the power source for the detecting voltage to be applied between the inner detecting pumping electrode and the outer detecting pumping electrode of the detecting pumping means.

Accordingly, any one of the pumping electrodes of the main pumping means is used in common with (shared with) the outer detecting pumping electrode of the detecting pumping means. When the common electrode is connected, for example, to the GND line, it is possible to use a non-insulated type power source based on the use of semiconductor components, as a power source for driving the detecting pumping means.

According to another aspect of the present invention, there is provided a gas sensor comprising a main pumping means for pumping-processing oxygen contained in a measurement gas introduced from external space into a processing space formed and comparted by a solid electrolyte contacting with the external space so that a partial pressure of oxygen in the processing space is controlled to have a predetermined value at which a predetermined gas component as a measurement objective is not decomposable; and a concentration-detecting means for decomposing the predetermined gas component contained in the measurement gas after being pumping-processed by the main pumping means by the aid of a catalytic action, and generating an electromotive force corresponding to a difference between an amount of oxygen produced by the decomposition and an amount of oxygen contained in a reference gas; wherein the predetermined gas component contained in the measurement gas is measured on the basis of the electromotive force detected by the concentration-detecting means; and the gas sensor further comprises an auxiliary pumping means for pumping out the oxygen contained in the measurement gas after being pumping-processed by the main pumping means toward an electrode which is fixed to have a base electric potential, of the main pumping means.

According to the present invention, at first, the oxygen, which is contained in the measurement gas introduced from the external space, is pumping-processed by the main pumping means, and the oxygen is adjusted to have a predetermined concentration. The measurement gas, which has been adjusted for the concentration of oxygen by means of the main pumping means, is introduced into the concentration-detecting means in the next step. In the concentration-detecting means, the electromotive force of the oxygen concentration cell is generated between the inner detecting electrode and the outer detecting electrode, corresponding to the difference between the amount of oxygen produced by the decomposition of the predetermined gas component contained in the measurement gas and the amount of oxygen contained in the gas existing on the side of the outer detecting electrode. The electromotive force is detected by the voltage-detecting means. Thus, the predetermined gas component corresponding to the amount of oxygen is measured.

Especially, in the present invention, the measurement gas, which has been subjected to coarse adjustment for the oxygen concentration to have a predetermined concentration by the aid of the main pumping means, is further subjected to fine adjustment for the oxygen concentration by the aid of the auxiliary pumping means.

In general, when the oxygen concentration in the measurement gas in the external space is greatly changed (for example, from 0 to 20%), then the oxygen concentration distribution in the measurement gas to be introduced into the main pumping means is greatly changed, and the amount of oxygen to be introduced into the processing space for the concentration-detecting means is also changed.

During this process, the oxygen concentration in the measurement gas after being pumping-processed by the main pumping means is finely adjusted in accordance with the pumping process effected by the auxiliary pumping means. However, owing to the pumping process performed by the main pumping means, the change in concentration of oxygen in the measurement gas introduced into the auxiliary pumping means is greatly reduced as compared with the change in concentration of oxygen in the measurement gas introduced from the external space (measurement gas introduced into the main pumping means). Accordingly, it is possible to accurately and constantly control the measurement of the predetermined gas component performed by the concentration-detecting means.

Therefore, the predetermined gas component introduced into the concentration-detecting means is scarcely affected by the change in concentration of oxygen in the measurement gas (measurement gas introduced into the main pumping means). As a result, the electromotive force generated in the concentration-detecting means is not affected by the change in oxygen concentration in the measurement gas, which has a value accurately corresponding to the predetermined gas component existing in the measurement gas.

Further, in the present invention, the auxiliary pumping means is operated to pump out the oxygen contained in the measurement gas after being pumping-processed by the main pumping means toward the electrode which is fixed to have the base electric potential, of the main pumping means. Accordingly, it is unnecessary to provide any DC power source which is insulated and independent from any other DC power source, in order to drive the auxiliary pumping means. Therefore, the detecting voltage can be generated by means of a non-insulated type power source which does not use any insulated type transformer. This consequently facilitates miniaturization of the control circuit system of the gas sensor and reduction of the weight thereof.

It is preferable that the main pumping means comprises the solid electrolyte contacting with the external space, and an inner main pumping electrode and an outer main pumping electrode formed on inner and outer surfaces of the solid electrolyte; the auxiliary pumping means comprises the solid electrolyte, and an inner auxiliary pumping electrode and an outer auxiliary pumping electrode formed in contact with the solid electrolyte; any one of the pumping electrodes of the main pumping means is used in common with the outer auxiliary pumping electrode of the auxiliary pumping means; and any one of the pumping electrodes is fixed to have the base electric potential.

In this embodiment, in order to pump out the oxygen by the aid of the auxiliary pumping means, an auxiliary voltage is applied between the inner auxiliary pumping electrode and the outer auxiliary pumping electrode, wherein a negative voltage is applied with respect to the inner main pumping electrode and the outer main pumping electrode of the main pumping means.

As a result, the reference line (line fixed at the base electric potential) can be commonly used for the power source for the control voltage to be applied between the inner main pumping electrode and the outer main pumping electrode of the main pumping means and the power source for the auxiliary voltage to be applied between the inner auxiliary pumping electrode and the outer auxiliary pumping electrode of the auxiliary pumping means.

Accordingly, any one of the pumping electrodes of the main pumping means is used in common with (shared with) the outer auxiliary pumping electrode of the auxiliary pumping means. When the common electrode is connected, for example, to the GND line, it is possible to use a non-insulated type power source based on the use of semiconductor components, as a power source for driving the auxiliary pumping means.

Preferably, the gas sensor constructed as described above further comprises a main pumping concentration-measuring means for generating an electromotive force corresponding to a difference between an amount of oxygen contained in a reference gas and an amount of oxygen contained in the measurement gas during the pumping process effected by the main pumping means; and a main pumping control means for controlling the pumping process effected by the main pumping means by adjusting a level of a control voltage applied between the inner main pumping electrode and the outer main pumping electrode of the main pumping means, on the basis of the electromotive force.

According to this embodiment, the main pumping concentration-measuring means is operated to generate the electromotive force corresponding to the difference between the amount of oxygen contained in the reference gas and the amount of oxygen contained in the measurement gas during the pumping process effected by the main pumping means. Further, the main pumping control means is operated to adjust the level of the control voltage applied between the inner main pumping electrode and the outer main pumping electrode of the main pumping means, on the basis of the electromotive force.

The main pumping means pumping-processes oxygen contained in the measurement gas introduced from the external space, in an amount corresponding to the level of the control voltage. The concentration of oxygen in the measurement gas is subjected to feedback control to be at a predetermined level in accordance with the supply of the level-adjusted control voltage to the main pumping means. During this process, for example, the partial pressure of oxygen in the processing atmosphere for the main pumping means is controlled to have a predetermined value at which the predetermined gas component is not decomposable.

Preferably, the gas sensor constructed as described above further comprises a detecting concentration-measuring means for generating an electromotive force corresponding to a difference between an amount of oxygen contained in a reference gas and an amount of oxygen produced during the decomposition of the predetermined gas component contained in the measurement gas after being pumping-processed by the main pumping means; and a detecting pumping control means for controlling the pumping process effected by the detecting pumping means by adjusting a level of a detecting voltage applied between the inner detecting pumping electrode and the outer detecting pumping electrode of the detecting pumping means, on the basis of the electromotive force.

According to this embodiment, the detecting concentration-measuring means is operated to generate the electromotive force corresponding to the difference between the amount of oxygen contained in the reference gas and the amount of oxygen produced during the decomposition of the predetermined gas component contained in the measurement gas after being pumping-processed by the main pumping means.

Further, the detecting pumping control means is operated to adjust the level of the detecting voltage applied between the inner detecting pumping electrode and the outer detecting pumping electrode of the detecting pumping means, on the basis of the electromotive force.

The detecting pumping means decomposes the predetermined gas component contained in the measurement gas after being pumping-processed by the main pumping means by the aid of the catalytic action and/or electrolysis, and the oxygen produced by the decomposition is pumping-processed, wherein feedback control is performed to give a predetermined value at which the predetermined gas component in the measurement gas is decomposable, in accordance with the supply of the level-adjusted detecting voltage to the detecting pumping means.

Preferably the gas sensor constructed as described above further comprises an auxiliary pumping means including the solid electrolyte and an inner auxiliary pumping electrode and an outer auxiliary pumping electrode formed in contact with the solid electrolyte, for pumping out oxygen contained in the measurement gas after being pumping-processed by the main pumping means toward the main pumping means.

According to this embodiment, the gas sensor includes the detecting pumping means and the auxiliary pumping means. The measurement gas, which has been subjected to coarse adjustment for the oxygen concentration to have a predetermined concentration by the aid of the main pumping means, is further subjected to fine adjustment for the oxygen concentration by the aid of the auxiliary pumping means.

Therefore, the predetermined gas component introduced into the detecting pumping means is scarcely affected by the change in concentration of oxygen in the measurement gas (measurement gas introduced into the main pumping means). As a result, the pumping current flowing through the detecting pumping means is not affected by the change in oxygen concentration in the measurement gas, which has a value accurately corresponding to the predetermined gas component existing in the measurement gas.

Preferably, the gas sensor constructed as described above further comprises an auxiliary concentration-measuring means for generating an electromotive force corresponding to a difference between the amount of oxygen contained in the reference gas and an amount of oxygen contained in the measurement gas after being pumping-processed by the main pumping means; and an auxiliary pumping control means for controlling the pumping process effected by the auxiliary pumping means by adjusting a level of an auxiliary pumping voltage applied between the inner auxiliary pumping electrode and the outer auxiliary pumping electrode of the auxiliary pumping means, on the basis of the electromotive force.

According to this embodiment, the auxiliary concentration-measuring means is operated to generate the electromotive force corresponding to the difference between the amount of oxygen contained in the reference gas and the amount of oxygen contained in the measurement gas after being pumping-processed by the main pumping means. Further, the auxiliary pumping control means is operated to adjust the level of the auxiliary pumping voltage applied between the inner auxiliary pumping electrode and the outer auxiliary pumping electrode of the auxiliary pumping means, on the basis of the electromotive force.

The auxiliary pumping means pumping-processes oxygen contained in the measurement gas after being pumping-processed by the main pumping means, in an amount corresponding to the level of the auxiliary pumping voltage. The concentration of oxygen in the measurement gas is subjected to feedback control to be at a predetermined level in accordance with the supply of the level-adjusted auxiliary pumping voltage to the auxiliary pumping means.

In the gas sensor constructed as described above, it is desirable that the outer auxiliary pumping electrode of the auxiliary pumping means is used in common with the electrode which is fixed to have the base electric potential, of the main pumping means.

In this embodiment, in order to pump out the oxygen by the aid of the auxiliary pumping means, an auxiliary voltage is applied between the inner auxiliary pumping electrode and the outer auxiliary pumping electrode, wherein a negative voltage is applied with respect to the inner main pumping electrode and the outer main pumping electrode of the main pumping means.

As a result, the reference line (line fixed at the base electric potential) can be commonly used for the power source for the control voltage to be applied between the inner main pumping electrode and the outer main pumping electrode of the main pumping means and the power source for the auxiliary voltage to be applied between the inner auxiliary pumping electrode and the outer auxiliary pumping electrode of the auxiliary pumping means.

According to still another aspect of the present invention, there is provided a method for controlling a gas sensor comprising the steps of pumping-processing oxygen contained in a measurement gas introduced from external space into a processing space formed and comparted by a solid electrolyte contacting with the external space by using a main pumping means so that a partial pressure of oxygen in the processing space is controlled to have a predetermined value at which a predetermined gas component as a measurement objective is not decomposable; decomposing the predetermined gas component contained in the measurement gas after being pumping-processed by the main pumping means by the aid of a catalytic action and/or electrolysis by using a detecting pumping means to pumping-process oxygen produced during the decomposition; and measuring the predetermined gas component contained in the measurement gas on the basis of a pumping current flowing through the detecting pumping means in accordance with the pumping process performed by the detecting pumping means; wherein the oxygen to be pumped out by the detecting pumping means is pumped out toward an electrode which is fixed to have a base electric potential, of the main pumping means.

According to the present invention, the detecting pumping means is used to decompose the predetermined gas component contained in the measurement gas after being pumping-processed by the main pumping means in accordance with the catalytic action and/or electrolysis. The oxygen produced during the decomposition is pumping-processed, and the pumping current generate thereby is detected. Thus, the predetermined gas component corresponding to the amount of oxygen is measured.

Especially in the method for controlling the gas sensor according to the present invention, during the measurement of the predetermined gas component, the oxygen to be pumped out by the detecting pumping means is pumped out toward the electrode which is fixed to have the base electric potential, of the main pumping means. As a result, it is unnecessary to provide any DC power source which is insulated and independent from any other DC power source, in order to drive the detecting pumping means. Therefore, the driving voltage can be generated by means of a non-insulated type power source which does not use any insulated type transformer. This consequently facilitates miniaturization of the control circuit system of the gas sensor and reduction of the weight thereof.

Preferably, the method described above further comprises the steps of measuring an electromotive force corresponding to a difference between an amount of oxygen contained in a reference gas and an amount of the oxygen produced during the decomposition of the predetermined gas component contained in the measurement gas after being pumping-processed by the main pumping means, by using a detecting concentration-measuring means; and adjusting the pumping process performed by the detecting pumping means on the basis of the electromotive force measured by the detecting concentration-measuring means.

Preferably, the method described above further comprises the step of pumping out the oxygen contained in the measurement gas after being pumping-processed by the main pumping means toward the processing space for the main pumping means, by using an auxiliary pumping means.

According to still another aspect of the present invention, there is provided a method for controlling a gas sensor comprising the steps of pumping-processing oxygen contained in a measurement gas introduced from external space into a processing space formed and comparted by a solid electrolyte contacting with the external space by using a main pumping means so that a partial pressure of oxygen in the processing space is controlled to have a predetermined value at which a predetermined gas component as a measurement objective is not decomposable; decomposing the predetermined gas component contained in the measurement gas after being pumping-processed by the main pumping means by the aid of a catalytic action by using a concentration-detecting means to detect an electromotive force generated corresponding to a difference between an amount of oxygen contained in a reference gas and an amount of oxygen produced during the decomposition; and measuring the predetermined gas component contained in the measurement gas on the basis of the electromotive force detected by the concentration-detecting means; wherein the oxygen contained in the measurement gas after being pumping-processed by the main pumping means is pumped out by using an auxiliary pumping means toward an electrode which is fixed to have a base electric potential, of the main pumping means.

According to the present invention, the electromotive force of the oxygen concentration cell is generated between an inner detecting electrode and an outer detecting electrode of the concentration-detecting means corresponding to the difference between the amount of oxygen contained in the gas existing on the side of the outer detecting electrode and the amount of oxygen produced by the decomposition of the predetermined gas component contained in the measurement gas. The electromotive force is detected by a voltage-detecting means. Thus, the predetermined gas component corresponding to the amount of oxygen is measured.

During the measurement of the predetermined gas component, the measurement gas, which has been subjected to coarse adjustment for the oxygen concentration to have a predetermined concentration by the aid of the main pumping means, is further subjected to fine adjustment for the oxygen concentration by the aid of the auxiliary pumping means. Therefore, the predetermined gas component introduced into the concentration-detecting means is scarcely affected by the change in concentration of oxygen in the measurement gas (measurement gas introduced into the main pumping means). As a result, the electromotive force generated in the concentration-detecting means is not affected by the change in oxygen concentration in the measurement gas, which has a value accurately corresponding to the predetermined gas component existing in the measurement gas.

Moreover, in the present invention, the oxygen contained in the measurement gas after being pumping-processed by the main pumping means is pumped out by the aid of the auxiliary pumping means toward the electrode which is fixed to have the base electric potential, of the main pumping means. Accordingly, it is unnecessary to provide any DC power source which is insulated and independent from any other DC power source, in order to drive the auxiliary pumping means. Therefore, the driving voltage can be generated by means of a non-insulated type power source which does not use any insulated type transformer. This consequently facilitates miniaturization of the control circuit system of the gas sensor and reduction of the weight thereof.

Preferably, the method described above further comprises the steps of measuring an electromotive force corresponding to a difference between the amount of oxygen contained in the reference gas and an amount of oxygen contained in the measurement gas after being pumping processed by the main pumping means, by using an auxiliary concentration-measuring means; and adjusting the pumping process performed by the auxiliary pumping means on the basis of the electromotive force measured by the auxiliary concentration-measuring means.

Preferably, the method described above further comprises the steps of measuring an electromotive force corresponding to a difference between the amount of oxygen contained in the reference gas and an amount of oxygen contained in the measurement gas during the pumping process performed by the main pumping means, by using a main pumping concentration-measuring means; and adjusting the pumping process performed by the main pumping means on the basis of the electromotive force measured by the main pumping concentration-measuring means.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Explanation will be made below with reference to FIGS. 1 to 7 for several illustrative embodiments in which the gas sensor and the method for controlling the gas sensor according to the present invention are applied to gas sensors for measuring gas components such as NO, $NO_2$, $SO_2$, $CO_2$, and $H_2O$ contained, for example, in atmospheric air and exhaust gas discharged from vehicles or automobiles.

Figure 1:
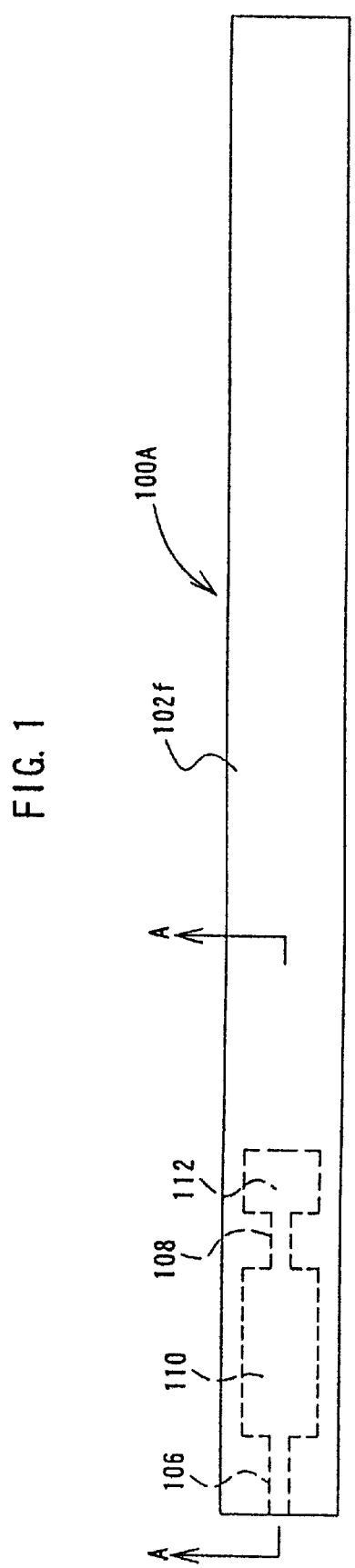
FIG. 1 shows a plan view illustrating a gas sensor according to a first embodiment.
Figure 2:
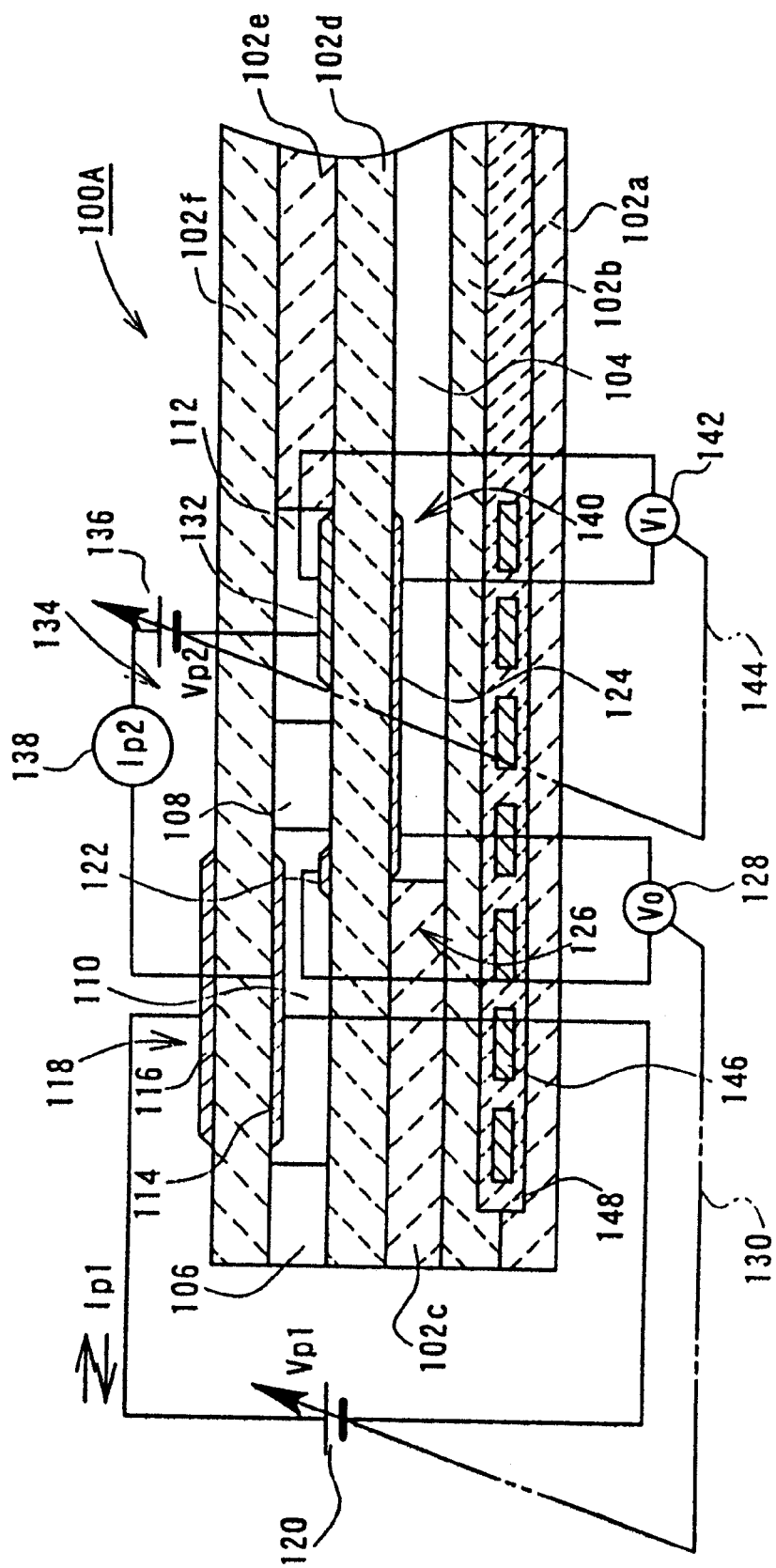
FIG. 2 shows a cross-sectional view (cross-sectional view taken along a line A—A shown in FIG. 1) illustrating the gas sensor according to the first embodiment.

At first, as shown in FIGS. 1 and 2, a gas sensor 100A according to a first embodiment is generally constructed to have a lengthy plate-shaped configuration comprising, for example, six stacked solid electrolyte layers 102a to 102f composed of ceramics based on the use of oxygen ion-conductive solid electrolytes such as $ZrO_2$. First and second layers from the bottom are designated as first and second substrate layers 102a, 102b respectively. Third and fifth layers from the bottom are designated as first and second spacer layers 102c, 102e respectively. Fourth and sixth layers from the bottom are designated as first and second solid electrolyte layers 102d, 102f respectively.

Specifically, the first spacer layer 102c is stacked on the second substrate layer 102b. The first solid electrolyte layer 102d, the second spacer layer 102e, and the second solid electrolyte layer 102f are successively stacked on the first spacer layer 102c.

A space (reference gas-introducing space) 104, into which a reference gas such as atmospheric air to be used as a reference for measuring oxides is introduced, is formed between the second substrate layer 102b and the first solid electrolyte layer 102d, the space 104 being comparted by a lower surface of the first solid electrolyte layer 102d, an upper surface of the second substrate layer 102b, and side surfaces of the first spacer layer 102c.

The second spacer layer 102e is interposed between the first and second solid electrolyte layers 102d, 102f. First and second diffusion rate-determining sections 106, 108 are also interposed between the first and second solid electrolyte layers 102d, 102f.

A first chamber 110 for adjusting the partial pressure of oxygen in a measurement gas is formed and comparted by a lower surface of the second solid electrolyte layer 102f, side surfaces of the first and second diffusion rate-determining sections 106, 108, and an upper surface of the first solid electrolyte layer 102d. A second chamber 112 for finely adjusting the partial pressure of oxygen in the measurement gas and measuring oxides, for example, nitrogen oxides (NOx) in the measurement gas is formed and comparted by a lower surface of the second solid electrolyte layer 102f, a side surface of the second diffusion rate-determining section 108, a side surface of the second spacer layer 102e, and an upper surface of the first solid electrolyte layer 102d.

The external space communicates with the first chamber 110 via the first diffusion-rate determining section 106, and the first chamber 110 communicates with the second chamber 112 via the second diffusion rate-determining section 108.

The first and second diffusion-rate determining sections 106, 108 give predetermined diffusion resistances to the measurement gas to be introduced into the first and second chambers 110, 112 respectively. Each of the first and second diffusion-rate determining sections 106, 108 can be formed as a passage composed of, for example, a porous material (for example, a porous compact composed of $ZrO_2$ or the like), or a small hole having a predetermined cross-sectional area so that the measurement gas may be introduced. Alternatively, each of the first and second diffusion-rate determining sections 106, 108 may be constructed by a gap layer or a porous layer produced by printing. In this embodiment, the comparative magnitude does not matter between the respective diffusion resistances of the first and second diffusion rate-determining sections 106, 108. However, it is preferable that the diffusion resistance of the second diffusion rate-determining section 108 is larger than that of the first diffusion rate-determining section 106.

The atmosphere in the first chamber 110 is introduced into the second chamber 112 under the predetermined diffusion resistance via the second diffusion rate-determining section 108.

An inner pumping electrode 114 having a substantially rectangular planar configuration and composed of a porous cermet electrode is formed on an entire lower surface portion for forming the first chamber 110, of the lower surface of the second solid electrolyte layer 102f. An outer pumping electrode 116 is formed on a portion corresponding to the inner pumping electrode 114, of the upper surface of the second solid electrolyte layer 102f. An electrochemical pumping cell, i.e., a main pumping cell 118 is constructed by the inner pumping electrode 114, the outer pumping electrode 116, and the second solid electrolyte layer 102f interposed between the both electrodes 114, 116.

A desired control voltage (pumping voltage) Vp1 is applied between the inner pumping electrode 114 and the outer pumping electrode 116 of the main pumping cell 118 by the aid of an external variable power source 120 to allow a pumping current Ip1 to flow in a positive direction or in a negative direction between the outer pumping electrode 116 and the inner pumping electrode 114. Thus, the oxygen in the atmosphere in the first chamber 110 can be pumped out to the external space, or the oxygen in the external space can be pumped into the first chamber 110.

A measuring electrode 122 having a substantially rectangular planar configuration and composed of a porous cermet electrode is formed in the close vicinity of the second diffusion rate-determining section 108 on an upper surface portion for forming the first chamber 110, of the upper surface of the first solid electrolyte layer 102d. A reference electrode 124 is formed on a lower surface portion exposed to the reference gas-introducing space 104, of the lower surface of the first solid electrolyte layer 102d. An electrochemical sensor cell, i.e., a controlling oxygen partial pressure-measuring cell 126 is constructed by the measuring electrode 122, the reference electrode 124, and the first solid electrolyte layer 102d.

The controlling oxygen partial pressure-measuring cell 126 is operated as follows. That is, an electromotive force is generated between the measuring electrode 122 and the reference electrode 124 on the basis of a difference in oxygen concentration between the atmosphere in the first chamber 110 and the reference gas (atmospheric air) in the reference gas-introducing space 104. The partial pressure oxygen in the atmosphere in the first chamber 110 can be detected by measuring the electromotive force by the aid of a voltmeter 128.

The voltage V0 generated between the reference electrode 124 and the measuring electrode 122 is an electromotive force of the oxygen concentration cell generated on the basis of the difference between the partial pressure of oxygen of the reference gas introduced into the reference gas-introducing space 104 and the partial pressure of oxygen of the measurement gas in the first chamber 110. The voltage V0 has the following relationship known as the Nernst's equation.

$$V0 = RT/4F \cdot \ln(P1(O_2)/P0(O_2))$$

R: gas constant;
T: absolute temperature;
F: Faraday constant;
$P1(O_2)$: partial pressure of oxygen in the first chamber 110;
$P0(O_2)$: partial pressure of oxygen in the reference gas.

Therefore, the partial pressure of oxygen in the first chamber 110 can be detected by measuring the voltage V0 generated on the basis of the Nernst's equation, by using the voltmeter 128.

The detected value of the partial pressure of oxygen is used to control the pumping voltage Vp1 of the variable power source 120 by the aid of a feedback control system 130. Specifically, the pumping operation effected by the main pumping cell 118 is controlled so that the partial pressure of oxygen in the atmosphere in the first chamber 110 has a predetermined value which is sufficiently low to control the partial pressure of oxygen in the second chamber 112 in the next step.

Each of the inner pumping electrode 114 and the outer pumping electrode 116 of the main pumping cell 118 and the measuring electrode 122 of the controlling oxygen partial pressure-measuring cell 126 is composed of an inert material having a low catalytic activity on NOx such as NO contained in the measurement gas introduced into the gas sensor 100A. Especially, the inner pumping electrode 114 and the measuring electrode 122 may be composed of a porous cermet electrode. In this embodiment, the electrode is composed of a metal such as Pt and a ceramic such as $ZrO_2$. It is necessary to use a material which has a weak reducing ability or no reducing ability with respect to the NO component in the measurement gas, for the inner pumping electrode 114 and the measuring electrode 122 disposed in the first chamber 110 to make contact with the measurement gas. It is preferable that the inner pumping electrode 114 and the measuring electrode 122 are composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

A detecting electrode 132 having a substantially rectangular planar configuration and composed of a porous cermet electrode is formed on an upper surface portion for forming the second chamber 112, of the upper surface of the first solid electrolyte layer 102d. An electrochemical pumping cell, i.e., a detecting pumping cell 134 is constructed by the detecting electrode 132, the inner pumping electrode 114 of the main pumping cell 118, the first solid electrolyte layer 102d, the second spacer layer 102e, and the second solid electrolyte layer 102f.

The detecting electrode 132 is composed of a porous cermet comprising Rh as a metal capable of reducing NOx as the measurement gas component and zirconia as a ceramic. Accordingly, the detecting electrode 132 functions as an NOx-reducing catalyst for reducing NOx existing in the atmosphere in the second chamber 112. Further, when a detecting voltage Vp2 is applied between the detecting electrode 132 and the inner pumping electrode 114 by the aid of a variable power source 136, the oxygen in the atmosphere in the second chamber 112 can be pumped out to the first chamber 110. The pumping current Ip2, which flows in accordance with the pumping action of the detecting pumping cell 134, is detected by an ammeter 138.

In the gas sensor 100A according to the first embodiment, an electrochemical sensor cell, i.e., a detection-controlling oxygen partial pressure-measuring cell 140 is constructed by the detecting electrode 132, the reference electrode 124, and the first solid electrolyte layer 102d.

The detection-controlling oxygen partial pressure-measuring cell 140 is operated as follows in the same manner as the controlling oxygen partial pressure-measuring cell 126. That is, an electromotive force V1 is generated between the detecting electrode 132 and the reference electrode 124 on the basis of a difference in oxygen concentration between the atmosphere in the second chamber 112 and the reference gas (atmospheric air) in the reference gas-introducing space 104. The value of the partial pressure of oxygen in the atmosphere in the second chamber 112 can be detected by measuring the electromotive force V1 by the aid of a voltmeter 142.

The detected value of the partial pressure of oxygen is used to control the detecting voltage Vp2 of the variable power source 136 by the aid of a feedback control system 144. Specifically, the detecting voltage Vp2 is controlled to have a voltage value at which the oxygen produced from NOx decomposed by the detecting electrode 132 can be sufficiently pumped out to the outside of the second chamber 112.

In this embodiment, the change in the amount of oxygen introduced into the second chamber 112 is greatly reduced as compared with the change in the amount of oxygen in the measurement gas, owing to the operation of the main pumping cell 118 for the first chamber 110. Accordingly, the partial pressure of oxygen in the second chamber 112 is controlled accurately and constantly.

The gas sensor 100A according to the first embodiment further comprises a heater 146 for generating heat in accordance with electric power supply from the outside. The heater 146 is embedded in a form of being vertically interposed between the first and second substrate layers 102a, 102b. The heater 146 is provided in order to increase the conductivity of oxygen ion. An insulative layer 148 composed of alumina or the like is formed to cover upper and lower surfaces of the heater 146 so that the heater 146 is electrically insulated from the substrate layers 102a, 102b.

As shown in FIG. 2, the heater 146 is arranged over the entire portion ranging from the first chamber 110 to the second chamber 112. Accordingly, each of the first chamber 110 and the second chamber 112 is heated to a predetermined temperature. Simultaneously, each of the main pumping cell 118, the controlling oxygen partial pressure-measuring cell 126, and the detecting pumping cell 134 is also heated to a predetermined temperature and maintained at that temperature.

The gas sensor 100A according to the first embodiment is basically constructed as described above. Next, its function and effect will be explained.

Prior to the measurement of the nitrogen oxide, the gas sensor 100A according to the first embodiment is set to be in a state in which the measurement gas can be introduced into the first chamber 110. Subsequently, an electric power is applied to the heater 146 to heat, for example, the first and second solid electrolyte layers 102d, 102f of the first chamber 110 in the gas sensor 100A to 700° C. to 900° C. and heat the first and second solid electrolyte layers 102d, 102f of the second chamber 112 to 400° C. to 900° C. The first and second solid electrolyte layers 102d, 102f are activated into desired states by heating the gas sensor 100A to be in the temperature state as described above.

Next, the measurement gas is introduced into the gas sensor 100A having been set as described above to start the measurement of the oxide such as NOx contained in the measurement gas.

The measurement gas is introduced into the first chamber 110 under the predetermined diffusion resistance through the first diffusion rate-determining section 106. The partial pressure of oxygen contained in the measurement gas is controlled to have a predetermined value in accordance with the pumping voltage Vp1 applied between the inner pumping electrode 114 and the outer pumping electrode 116 by the aid of the variable power source 120. That is, the partial pressure of oxygen in the first chamber 110 can be measured on the basis of the voltage V0 between the reference electrode 124 and the measuring electrode 122 detected by the voltmeter 128 of the controlling oxygen partial pressure-measuring cell 126. The voltage V0 is the electromotive force of the oxygen concentration cell specified by the Nernst's equation described above. The pumping voltage Vp1 of the variable power source 120 is controlled by the aid of the feedback control system 130 so that the voltage V0 is 150 mV to 350 mV. Thus, the partial pressure of oxygen in the first chamber 110 is controlled to have a predetermined value.

The measurement gas, which has been controlled to have the predetermined partial pressure of oxygen in the first chamber 110, is introduced into the second chamber 112 through the second diffusion rate-determining section 108 which is set to have a diffusion resistance larger than that of the first diffusion rate-determining section 106.

In the second chamber 112, the detecting voltage Vp2, which is controlled to have a voltage value to make it possible to sufficiently pump out oxygen in the second chamber 112, is applied between the detecting electrode 132 and the inner pumping electrode 114 by the aid of the variable power source 136 (controlled by the electromotive force V1). NOx such as NO and $NO_2$ contained in the measurement gas is decomposed by the detecting electrode 132 as the oxide-decomposing catalyst composed of the Rh cermet by the aid of the detecting voltage Vp2, or NOx is decomposed by the catalyst disposed separately from the detecting electrode 132. The oxygen generated thereby is pumped out toward the first chamber 110 through the second solid electrolyte layer 102f. During this process, the current value Ip2, which is generated by the movement of oxygen ion, is measured by the ammeter 138. The concentration of the predetermined oxide, for example, NOx such as NO and $NO_2$ contained in the measurement gas is measured from the current value Ip2.

Next, explanation will be made with reference to FIG. 3 for a control circuit system 150A (hereinafter simply referred to as "control circuit system according to the first embodiment) of the gas sensor 100A according to the first embodiment.

Figure 3:
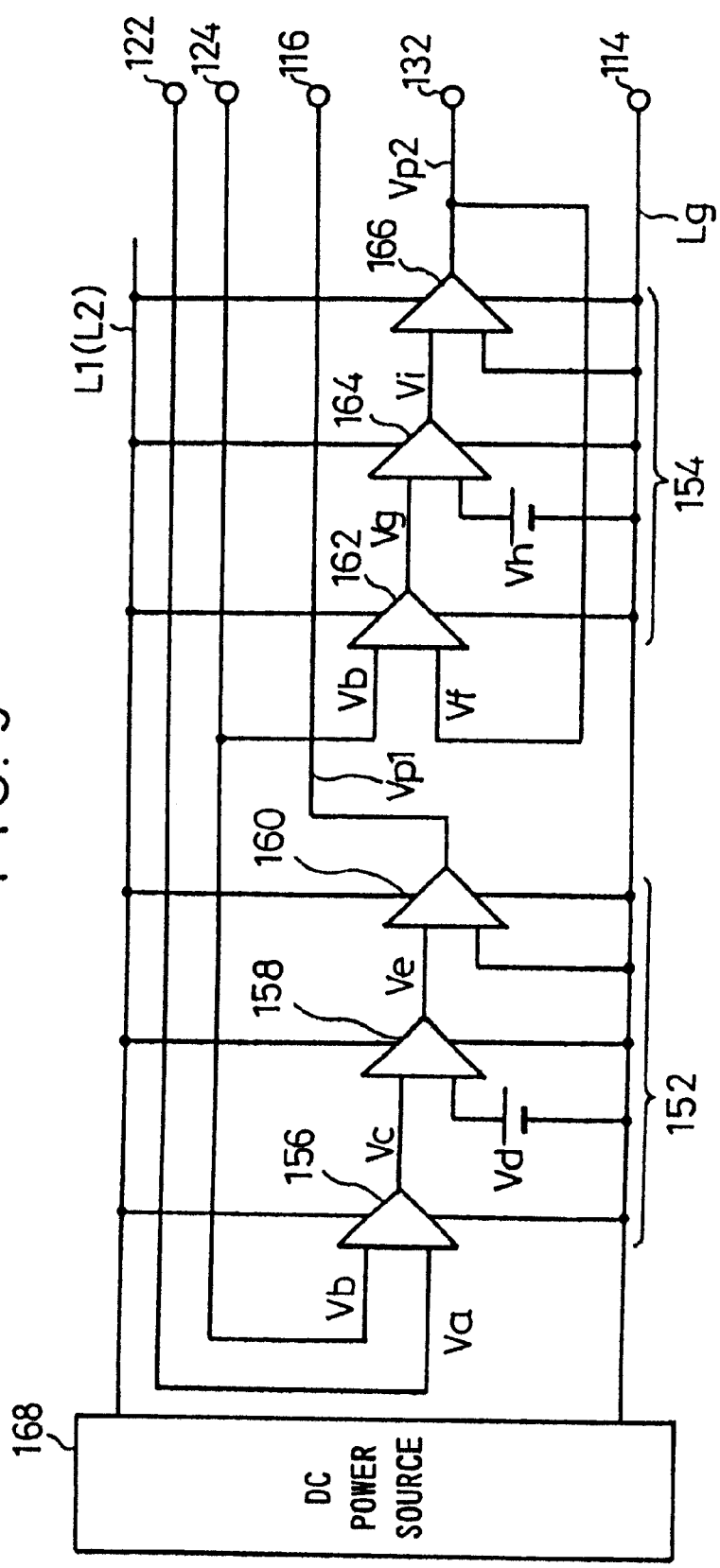
FIG. 3 shows a circuit diagram illustrating a control circuit system concerning the first embodiment.

As shown in FIG. 3, the control circuit system 150A according to the first embodiment comprises a main pumping control circuit 152 and a detecting pumping control circuit 154.

The main pumping control circuit 152 comprises a first comparator 156 for determining a difference between the difference (measured voltage Va) between the electric potential of the measuring electrode 122 and the ground electric potential and the difference (reference voltage Vb) between the electric potential of the reference electrode 124 and the ground electric potential, a second comparator 158 for determining a difference between an output Vc of the first comparator 156 and a target voltage Vd (for example, 300 mV), and a first amplifier 160 for amplifying an output Ve of the second comparator 158 with a predetermined gain and outputting an obtained voltage as the pumping voltage Vp1 to the outer pumping electrode 116.

The detecting pumping control circuit 154 comprises a third comparator 162 for determining a difference between the difference (detection voltage Vf) between the electric potential of the detecting electrode 132 and the ground electric potential and the difference (reference voltage Vb) between the electric potential of the reference electrode 124 and the ground electric potential, a fourth comparator 164 for determining a difference between an output Vg of the third comparator 162 and a target voltage Vh (for example, 450 mV), and a second amplifier 166 for amplifying an output Vi of the fourth comparator 164 with a predetermined gain and outputting an obtained voltage as the detecting voltage Vp2 to the detecting electrode 132.

Each of the first comparator 156, the second comparator 158, and the first amplifier 160 for constructing the main pumping control circuit 152, and the third comparator 162, the fourth comparator 164, and the second amplifier 166 for constructing the detecting pumping control circuit 154 is composed of an operational amplifier. As for each of them, one power source terminal is connected to a positive (+) side power source line L1 or a negative (−) side power source line L2 led from a DC power source 168, and the other power source terminal is connected to a GND line Lg led from the DC power source 168. The inner pumping electrode 114 is connected to the GND line Lg.

Accordingly, as for the main pumping control circuit 152, at first, the measurement gas is introduced into the first chamber 110 via the first diffusion rate-determining section 106, and the measured voltage Va and the reference voltage Vb obtained during this process are supplied to the first comparator 156. The differential voltage Vc between the measured voltage Va and the reference voltage Vb is outputted from the first comparator 156. The differential voltage Vc is applied, for example, to an inverting terminal of the second comparator 158 disposed at the downstream stage. The second comparator 158 determines the difference between the differential voltage Vc supplied to the inverting terminal and the target voltage Vd (for example, 300 mV) supplied to the non-inverting terminal. The voltage signal Ve, which represents the difference, is outputted from the output terminal. The voltage signal Ve is amplified with the predetermined gain by the first amplifier 160 disposed at the downstream stage, and the amplified voltage is supplied as the pumping voltage Vp1 to the outer pumping electrode 116 of the main pumping cell 118. In this embodiment, the inner pumping electrode 114 is connected to the GND line Lg to have the ground electric potential (0 V). Therefore, the voltage between the both electrodes 114, 116 of the main pumping cell 118 is consequently equivalent to the pumping voltage Vp1 supplied from the first amplifier 160.

In this embodiment, the DC power source 158 has the positive/negative (±) output. When the oxygen concentration the first chamber 110 is lower than the target oxygen concentration, a negative voltage is applied to the outer pumping electrode 116. Thus, the oxygen in the external space is pumped into the first chamber 110. On the contrary, when the oxygen concentration in the first chamber 110 is higher than the target oxygen concentration, a positive voltage is applied to the outer pumping electrode 116. Thus, the oxygen in the first chamber 110 is pumped out to the external space.

That is, the main pumping cell 118 pumps out the oxygen contained in the measurement gas introduced into the first chamber 110 in an amount corresponding to the level of the pumping voltage Vp1, or the main pumping cell 118 pumps in the oxygen in an amount corresponding to the level of the pumping voltage Vp1. The series of operations are repeated, and thus the oxygen concentration in the first chamber 110 is subjected to feedback control to achieve the predetermined level.

On the other hand, as for the detecting pumping control circuit 154, the measurement gas in the first chamber 110 is introduced into the second chamber 112 via the second diffusion rate-determining section 108. The detection voltage Vf and the reference voltage Vb obtained during this process are supplied to the third comparator 162. The differential voltage Vg between the detection voltage Vf and the reference voltage Vb is outputted from the third comparator 162. The differential voltage Vg is applied, for example, to an inverting terminal of the fourth comparator 164 disposed at the downstream stage. The fourth comparator 164 determines the difference between the differential voltage Vg supplied to the inverting terminal and the target voltage Vh (for example, 450 mV) supplied to the non-inverting terminal. The voltage signal Vi, which represents the difference, is outputted from the output terminal. The voltage signal Vi is amplified with the predetermined gain by the second amplifier 166 disposed at the downstream stage, and the amplified voltage is supplied as the detecting voltage Vp2 to the detecting electrode 132 of the detecting pumping cell 134. In this embodiment, the inner pumping electrode 114 is connected to the GND line Lg to have the ground electric potential (0 V). Therefore, the voltage between the both electrodes 114, 132 of the detecting pumping cell 134 is consequently equivalent to the detecting voltage Vp2 supplied from the second amplifier 166.

In this embodiment, the target oxygen concentration in the second chamber 112 is set to be lower than the target oxygen concentration in the first chamber 110. Therefore, a negative voltage is applied to the detecting electrode 132. Accordingly, the oxygen in the second chamber 112 is pumped out through the second solid electrolyte layer 102f to the first chamber 110.

As described above, in the gas sensor 100A according to the first embodiment, the oxygen to be pumped out by using the detecting pumping cell 134 is pumped out toward the inner pumping electrode 114 connected to the GND line Lg of the DC power source 168, of the inner pumping electrode 114 and the outer pumping electrode 116 of the main pumping cell 118. That is, the oxygen is pumped out to the inside of the first chamber 110. Therefore, when the oxygen is pumped out by the aid of the detecting pumping cell 134, the negative voltage is applied to the detecting electrode 132.

Accordingly, the reference line (GND line Lg) of the power source for the pumping voltage Vp1 to be applied between the outer pumping electrode 116 and the inner pumping electrode 114 of the main pumping cell 118 can be used in common with that of the power source for the detecting voltage Vp2 to be applied between the detecting electrode 132 and the inner pumping electrode 114 of the detecting pumping cell 134.

As a result, it is unnecessary to prepare any separate DC power source which is insulated and independent (insulated type power source) in order to drive the detecting pumping cell 134. Therefore, the detecting voltage Vp2 can be generated by using the non-insulated type power source which does not use any insulated type transformer. This consequently facilitates miniaturization of the control circuit system 150A of the gas sensor 100A and reduction of the weight thereof. Further, this facilitates miniaturization of the gas sensor 100A itself and reduction of the weight thereof.

Especially, in the gas sensor 100A according to the first embodiment, the electrode, which serves as the reference for the electric potential in the main pumping cell 118, is used in common with the electrode which serves as the reference for the electric potential in the detecting pumping cell 134, namely, the both electrodes are commonly used as the inner pumping electrode 114. Therefore, when the inner pumping electrode 114 is connected to the GND line Lg as in this embodiment, it is possible to use the non-insulated type power source based on the use of semiconductor parts, as the power source for driving the detecting pumping cell 134.

Figure 10:
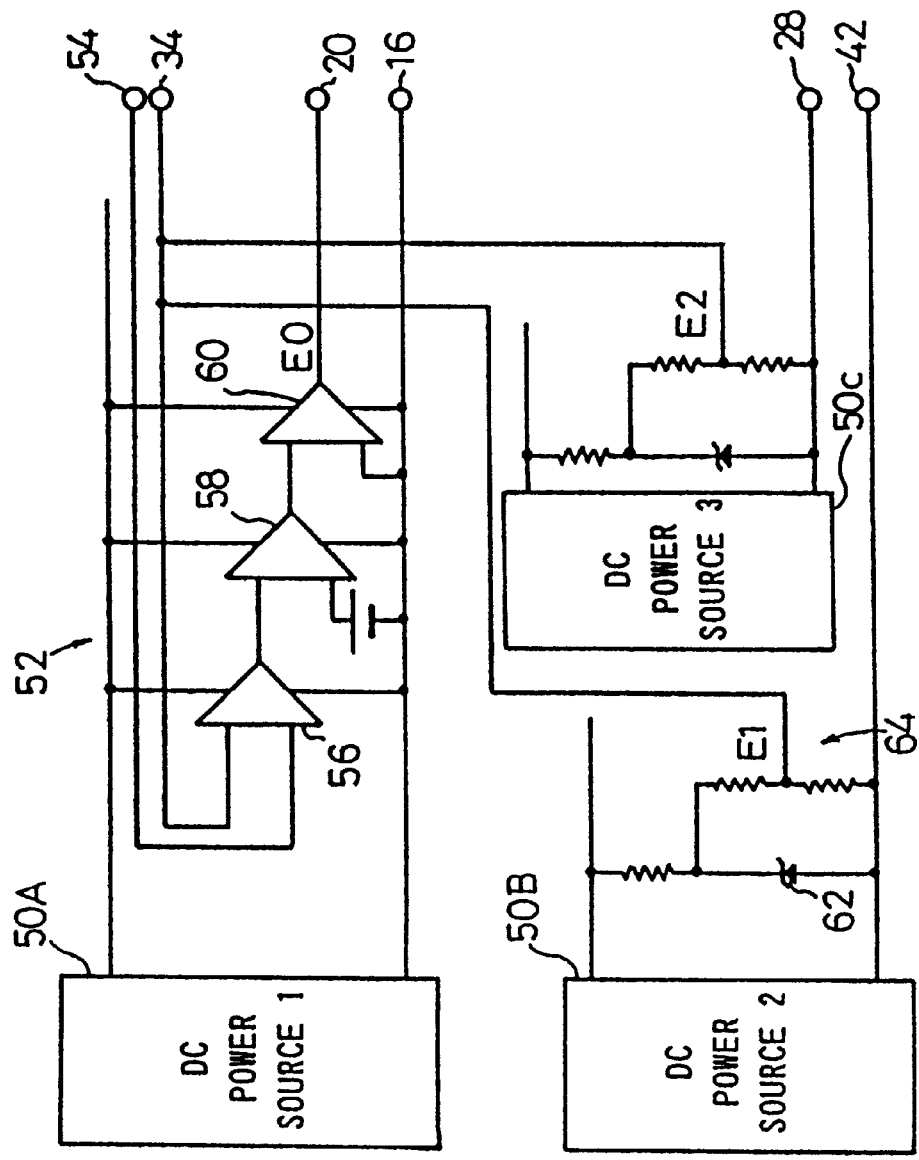
FIG. 10 shows a circuit diagram illustrating a control circuit system concerning the illustrative suggested example.
Figure 11:
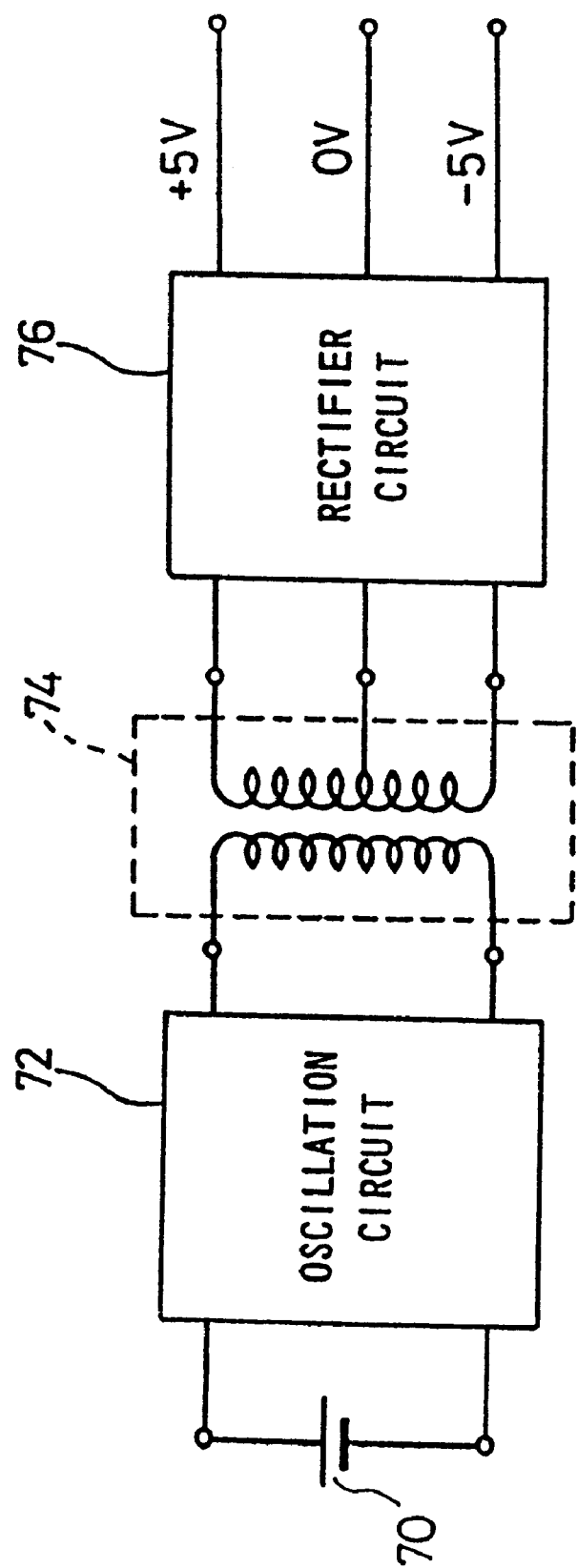
FIG. 11 shows a circuit diagram illustrating an example of a mutually insulated and independent DC power source.

In other words, in the case of the conventional technique as shown in FIG. 10, it has been necessary that DC power sources or DC-DC-converters connected to the DC power sources are prepared as a number of individuals corresponding to the control circuits (pumping control circuits 52) and power source voltage-generating circuits (circuits for generating voltages E1, E2). However, in the case of the gas sensor 100A according to the first embodiment, it is sufficient that the DC power source 168 or DC-DC converter is prepared as a number of individuals which is smaller than the number of the control circuits (the main pumping control circuit 152 and the detecting pumping control circuit 154). Especially, the electric power can be supplied from the power source to the respective control circuits (152, 154) by preparing only one DC power source 168 or only one DC-DC converter connected to one DC power source 168.

Next, explanation will be made for a modified embodiment of the gas sensor 100A according to the first embodiment with reference to FIG. 4. Components or parts corresponding to those shown in FIG. 2 are designated by the same reference numerals, duplicate explanation of which will be omitted.

Figure 4:
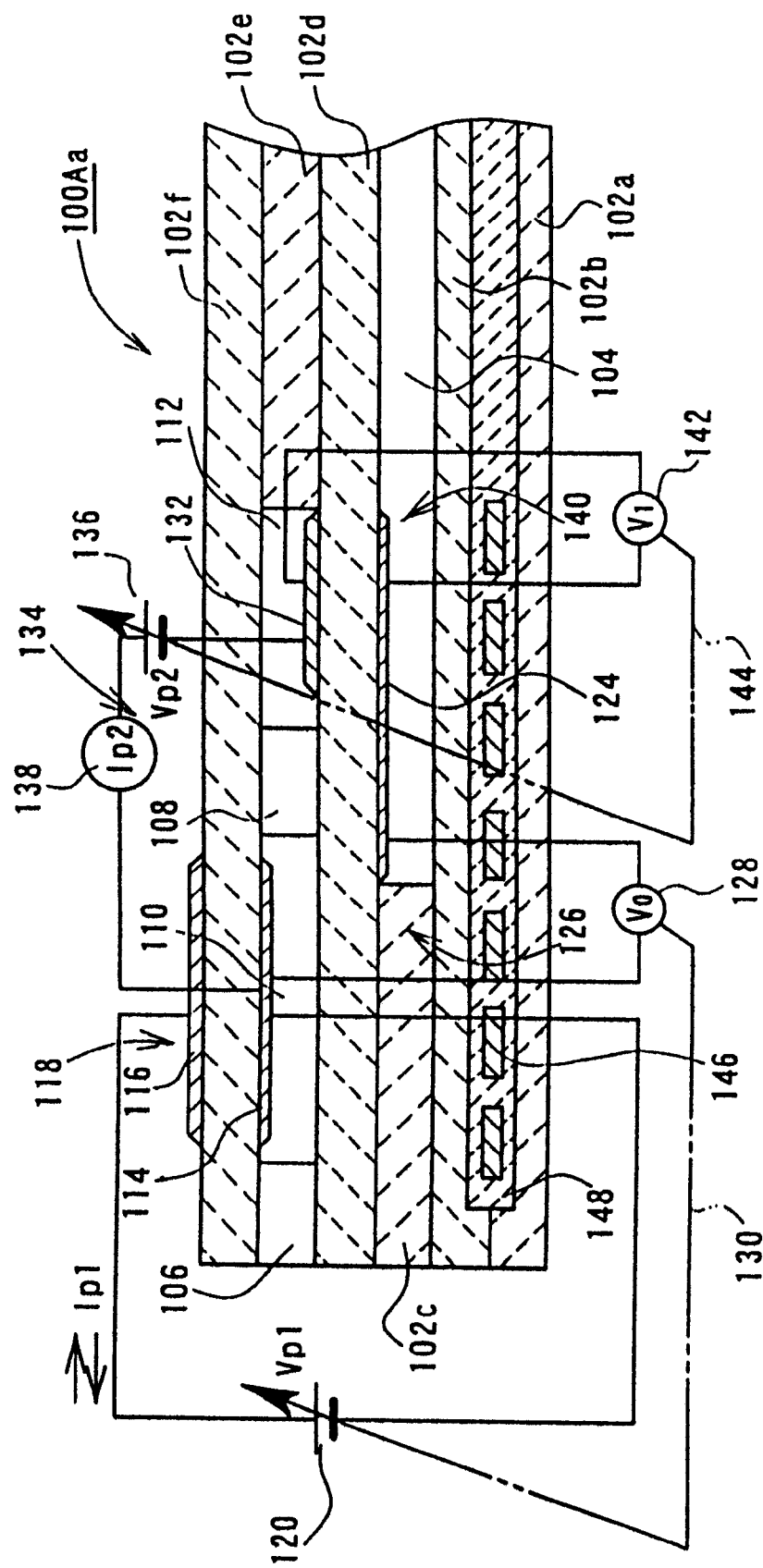
FIG. 4 shows a cross-sectional view illustrating a modified embodiment of the gas sensor according to the first embodiment.

As shown in FIG. 4, a gas sensor 100Aa according to this modified embodiment is constructed approximately in the same manner as the gas sensor 100A according to the first embodiment described above (see FIG. 2). However, the former is different from the latter in that the inner pumping electrode 114 of the main pumping cell 118 is used in common with the measuring electrode 122 of the controlling oxygen partial pressure-measuring cell 126 (see FIG. 2). Therefore, the gas sensor 100Aa according to this modified embodiment does not include the measuring electrode 122.

The operation of the gas sensor 100Aa according to this modified embodiment will be explained. At first, the measurement gas is introduced into the first chamber 110. During this process, the terminal voltage V0 between the inner pumping electrode 114 of the main pumping cell 118 and the reference electrode 124 formed on the side of the reference gas-introducing space 104 is measured by the voltmeter 128. The variable power source 120 is subjected to feedback control on the basis of the measured voltage V0. Accordingly, the pumping operation performed by the main pumping cell 118 is controlled so that the partial pressure of oxygen in the atmosphere in the first chamber 110 has a predetermined value which is sufficiently low to control the partial pressure of oxygen in the second chamber 112 in the next step.

In this embodiment, the measured voltage V0, which is detected by the voltmeter 128 of the controlling oxygen partial pressure-measuring cell 126, is the terminal voltage V0 between the inner pumping electrode 114 and the reference electrode 124. Therefore, when the amount of oxygen pumped out by the main pumping cell 118 is changed, and the oxygen concentration in the atmosphere in the first chamber 110 is changed, then the terminal voltage V0 between the reference electrode 124 and the inner pumping electrode 114 of the main pumping cell 118 is changed without any time delay. Accordingly, the feedback control system 130 for the variable power source 120 can control the oxygen concentration in the first chamber 110 highly accurately without causing any oscillation phenomenon.

The gas sensor 100Aa according to this modified embodiment suffers from an error in the measurement of the electromotive force performed by the controlling oxygen partial pressure-measuring cell 126, of (interface resistance between inner pumping electrode 114 and second solid electrolyte layer 102f)×(pumping current Ip1 flowing through main pumping cell 118). Therefore, it is desirable that the target voltage Vd, which should be compared with the output Vc from the first comparator 156 in the second comparator 158 of the main pumping control circuit 152 shown in FIG. 3, is corrected to be a target voltage value in consideration of an amount of the error described above.

Next, explanation will be made for a gas sensor 100B according to a second embodiment with reference to FIG. 5. Components or parts corresponding to those shown in FIG. 2 are designated by the same reference numerals, duplicate explanation of which will be omitted.

Figure 5:
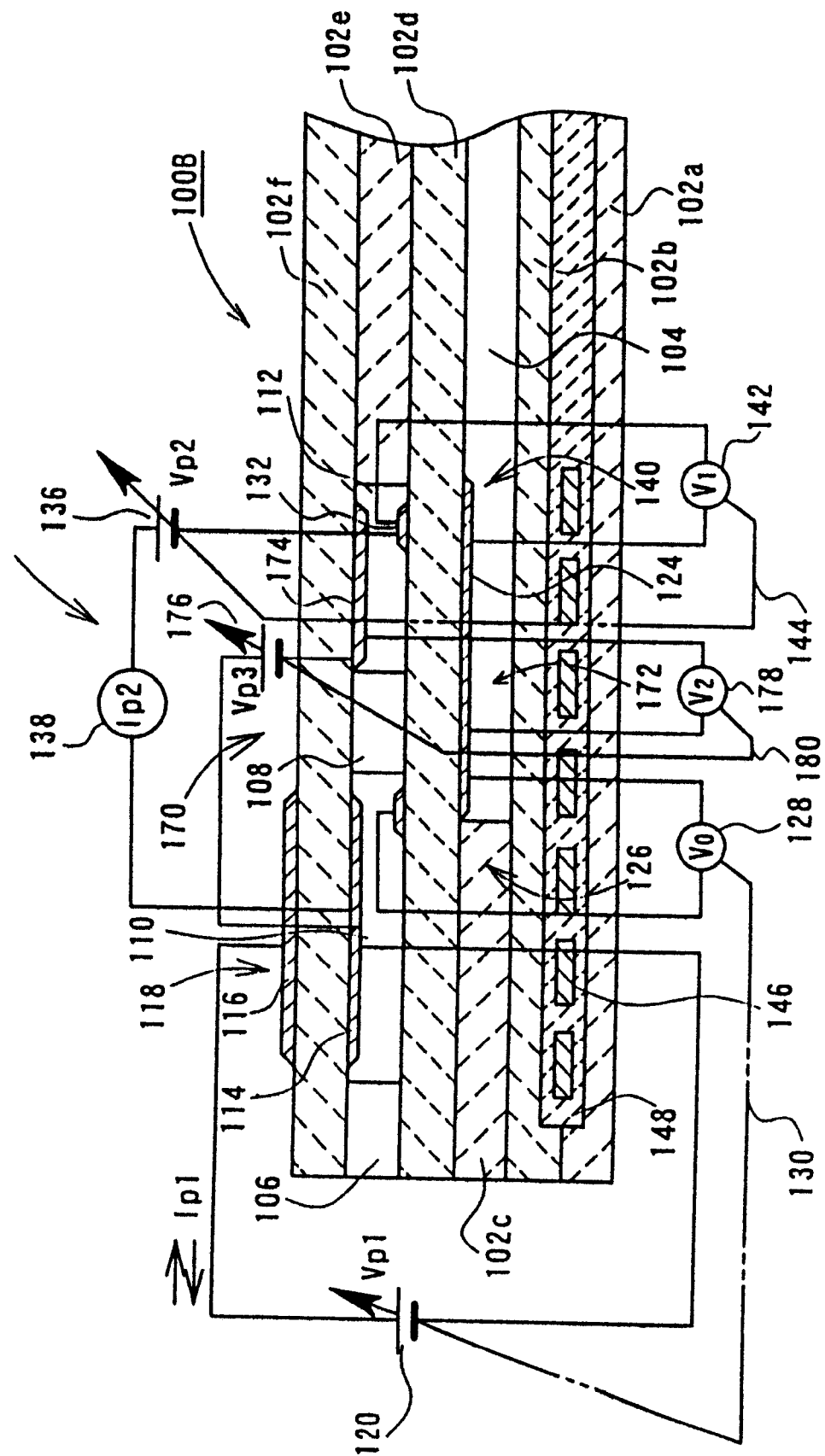
FIG. 5 shows a cross-sectional view illustrating a gas sensor according to a second embodiment.

As shown in FIG. 5, the gas sensor 100B according to the second embodiment is constructed approximately in the same manner as the gas sensor 100A according to the first embodiment described above (see FIG. 2). However, the former is different from the latter in that an auxiliary pumping cell 170 and an auxiliary oxygen partial pressure-measuring cell 172 are provided.

The auxiliary pumping cell 170 is constructed by an auxiliary pumping electrode 174 having a substantially rectangular planar configuration and composed of a porous cermet electrode formed on an entire lower surface portion for forming the second chamber 112, of the lower surface of the second solid electrolyte layer 102f, the inner pumping electrode 114 of the main pumping cell 118, and the second solid electrolyte layer 102f.

The auxiliary pumping electrode 174 is based on the use of a material having a weak reducing ability or no reducing ability with respect to the NO component in the measurement gas, in the same manner as the inner pumping electrode 114 of the main pumping cell 118. In this embodiment, it is preferable that the auxiliary pumping electrode 174 is composed of, for example, a compound having the perovskite structure such as $La_3CuO_4$, a cermet comprising a ceramic and a metal such as Au having a low catalytic activity, or a cermet comprising a ceramic, a metal of the Pt group, and a metal such as Au having a low catalytic activity. When an alloy composed of Au and a metal of the Pt group is used as an electrode material, it is preferable to add Au in an amount of 0.03 to 35% by volume of the entire metal component.

The oxygen in the atmosphere in the second chamber 112 can be pumped out toward the first chamber 110 by applying an auxiliary pumping voltage Vp3 by the aid of a variable power source 176 between the auxiliary pumping electrode 174 and the inner pumping electrode 114 of the auxiliary pumping cell 170.

The auxiliary oxygen partial pressure-measuring cell 172 is constructed by the auxiliary pumping electrode 174, the reference electrode 124, the second solid electrolyte layer 102f, the second spacer layer 102e, and the first solid electrolyte layer 102d.

The auxiliary oxygen partial pressure-measuring cell 172 is operated as follows in the same manner as the controlling oxygen partial pressure-measuring cell 126 described above. That is, the partial pressure of oxygen in the atmosphere in the second chamber 112 can be detected by measuring an electromotive force V2 generated between the auxiliary pumping electrode 174 and the reference electrode 124 by using a voltmeter 178 on the basis of a difference in oxygen concentration between the atmosphere in the second chamber 112 and the reference gas (atmospheric air) in the reference gas-introducing space 104.

The detected value of the partial pressure of oxygen is used to control the auxiliary pumping voltage Vp3 of the variable power source 176 by the aid of a feedback control system 180. The control is performed so that the partial pressure of oxygen in the atmosphere in the second chamber 112 is in a condition under which the measurement gas component (NOx) is not substantially reducible or decomposable, and the partial pressure of oxygen has a low value at which the measurement of the amount of the objective component is not substantially affected. Specifically, the variable power source 176 is controlled at a voltage value having a magnitude to give a limiting current to the pumping operation for the oxygen produced during the decomposition effected by the auxiliary pumping cell 170. In this embodiment, when the amount of oxygen pumped out by the auxiliary pumping cell 170 is changed, and the oxygen concentration in the atmosphere in the second chamber 112 is changed, then the terminal voltage V2 between the auxiliary pumping electrode 174 and the reference electrode 124 is changed without any time delay. Accordingly, the feedback control system 180 for the variable power source 176 can control the oxygen concentration in the second chamber 112 highly accurately without causing any oscillation phenomenon.

When it is intended to control the partial pressure of oxygen in the atmosphere in the first chamber 110 to have a low value of the partial pressure of oxygen which does not substantially affect the measurement of NOx, by operating the main pumping cell 118, in other words, when the pumping voltage Vp1 of the variable power source 120 is adjusted by the aid of the feedback control system 130 so that the voltage V0 detected by the controlling oxygen partial pressure-detecting cell 126 is constant, if the oxygen concentration in the measurement gas greatly changes, for example, in a range of 0 to 20%, then the respective partial pressures of oxygen in the atmosphere in the second chamber 112 and in the atmosphere in the vicinity of the detecting electrode 132 slightly change in ordinary cases. This phenomenon is caused probably because of the following reason. That is, when the oxygen concentration in the measurement gas increases, the distribution of the oxygen concentration occurs in the widthwise direction and the thickness direction over the measuring electrode 122 in the first chamber 110. The distribution of the oxygen concentration changes depending on the oxygen concentration in the measurement gas.

However, in the case of the gas sensor 100B according to the second embodiment, the auxiliary pumping cell 170 is provided for the second chamber 112 so that the partial pressure of oxygen in its internal atmosphere always has a constant low value of the partial pressure of oxygen. Accordingly, even when the partial pressure of oxygen in the atmosphere introduced from the first chamber 110 into the second chamber 112 changes depending on the oxygen concentration in the measurement gas, the partial pressure of oxygen in the atmosphere in the second chamber 112 can be always made to have a constant low value, owing to the pumping operation performed by the auxiliary pumping cell 170. As a result, the partial pressure of oxygen can be controlled to have a low value at which the measurement of NOx is not substantially affected.

NOx in the measurement gas introduced into the detecting electrode 132 is reduced or decomposed around the detecting electrode 132. Thus, for example, a reaction of NO→½N$_2$+½O$_2$ is allowed to occur. In this process, a predetermined voltage Vp2, for example, 430 mV (700° C.) is applied between the detecting electrode 132 and the inner pumping electrode 114 for constructing the detecting pumping cell 134, in a direction to pump out the oxygen from the second chamber 112 to the first chamber 110.

Therefore, the pumping current Ip2 flowing through the detecting pumping cell 134 has a value which is proportional to a sum of the oxygen concentration in the atmosphere introduced into the second chamber 112, i.e., the oxygen concentration in the second chamber 112 and the oxygen concentration produced by reduction or decomposition of NOx by the aid of the detecting electrode 132.

In this embodiment, the oxygen concentration in the atmosphere in the second chamber 112 is controlled to be constant by means of the auxiliary pumping cell 172. Accordingly, the pumping current Ip2 flowing through the detecting pumping cell 134 is proportional to the NOx concentration. Further, when an alumina film for constructing a third diffusion rate-determining section (not shown) is formed to cover the detecting electrode 132 therewith, the NOx concentration corresponds to the amount of diffusion of NOx limited by the third diffusion rate-determining section. Therefore, even when the oxygen concentration in the measurement gas greatly changes, it is possible to accurately measure the NOx concentration, based on the use of the detecting pumping cell 134 by the aid of the ammeter 138.

It is assumed, for example, that the partial pressure of oxygen in the atmosphere in the second chamber 112 controlled by the auxiliary pumping cell 170 is 0.02 ppm, and the concentration of NO as the NOx component in the measurement gas is 100 ppm. The pumping current Ip2 flows in an amount corresponding to a sum (=50.02 ppm) of an oxygen concentration of 50 ppm produced by reduction or decomposition of NO and the oxygen concentration of 0.02 ppm in the atmosphere in the second chamber 112. Therefore, almost all of the pumping current value Ip2 obtained by operating the detecting pumping cell 134 represents the amount brought about by the reduction or decomposition of NO. Accordingly, the obtained result does not depend on the oxygen concentration in the measurement gas.

Next, explanation will be made with reference to FIG. 6 for a control circuit system 150B (hereinafter simply referred to as "control circuit system according to the second embodiment) of the gas sensor 100B according to the second embodiment. Components or parts corresponding to those shown in FIG. 3 are designated by the same reference numerals, duplicate explanation of which will be omitted.

Figure 6:
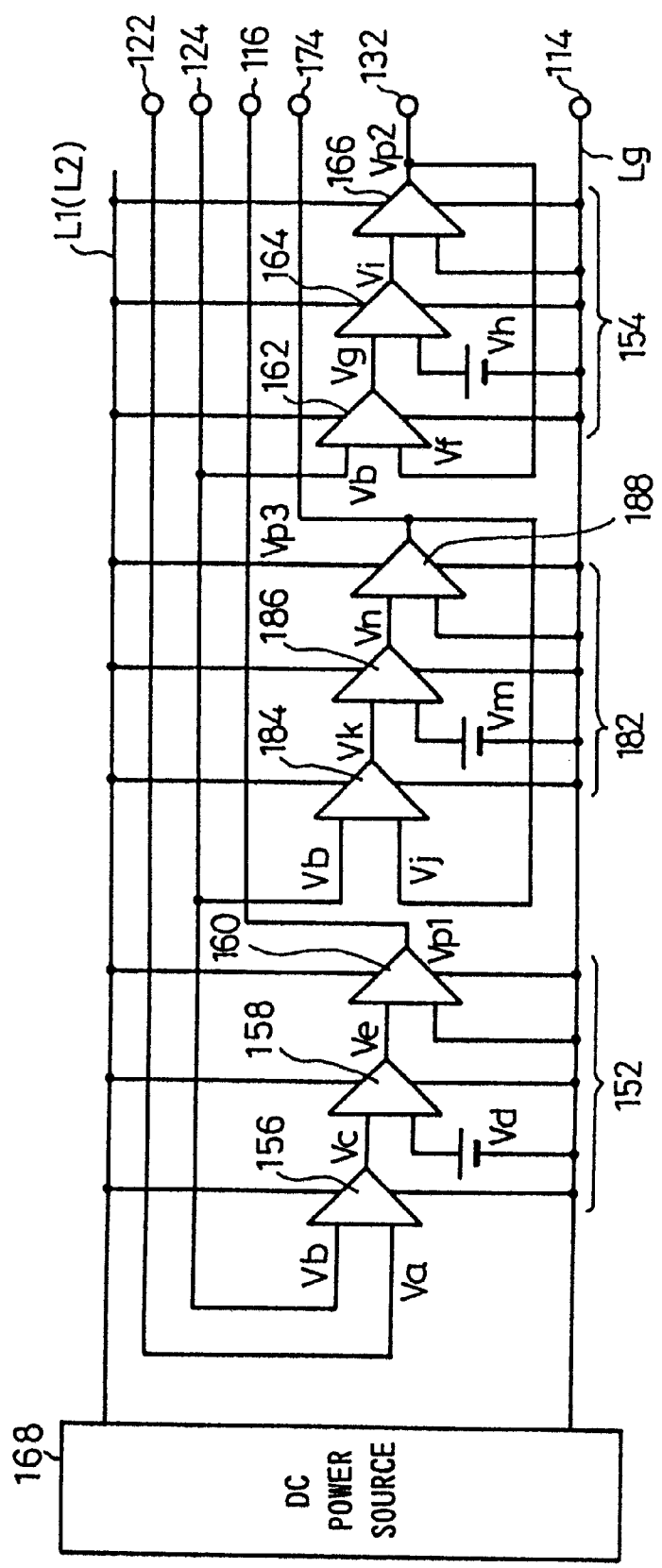
FIG. 6 shows a circuit diagram illustrating a control circuit system concerning the second embodiment.

As shown in FIG. 6, the control circuit system 150B according to the second embodiment is constructed in approximately the same manner as the control circuit system 150A according to the first embodiment described above (see FIG. 3). However, the former is different from the latter in that the auxiliary pumping cell 170 is added, and hence an auxiliary pumping control circuit 182 for controlling the auxiliary pumping cell 170 is inserted and connected between the main pumping control circuit 152 and the detecting pumping control circuit 154.

As shown in FIG. 6, the auxiliary pumping control circuit 182 comprises a fifth comparator 186 for determining a difference between the difference (detection voltage Vj) between the electric potential of the auxiliary pumping electrode 174 and the ground electric potential and the difference (reference voltage Vb) between the electric potential of the reference electrode 124 and the ground electric potential, a sixth comparator 186 for determining a difference between an output Vk of the fifth comparator 184 and a target voltage Vm (for example, 450 mV), and a third amplifier 188 for amplifying an output Vn of the sixth comparator 186 with a predetermined gain and outputting an obtained voltage as the auxiliary pumping voltage Vp3 to the auxiliary pumping electrode 174.

Each of the fifth comparator 184, the sixth comparator 186., and the third amplifier 188 is composed of an operational amplifier in the same manner as the first comparator 156, the second comparator 158, and the first amplifier 160 for constructing the main pumping control circuit 152, and the third comparator 162, the fourth comparator 164, and the second amplifier 166 for constructing the detecting pumping control circuit 154. As for each of them, one power source terminal is connected to the positive (+) side power source line L1 or the negative (−) side power source line L2 led from the DC power source 168, and the other power source terminal is connected to the GND line Lg led from the DC power source 168. Also in this embodiment, the inner pumping electrode 114 is connected to the GND line Lg.

Accordingly, as for the auxiliary pumping control circuit 182, the measurement gas in the first chamber 110 is introduced into the second chamber 112 via the second diffusion rate-determining section 108, and the detection voltage Vj and the reference voltage Vb obtained during this process are supplied to the fifth comparator 184. The differential voltage Vk between the detection voltage Vj and the reference voltage Vb is outputted from the fifth comparator 184. The differential voltage Vk is applied, for example, to an inverting terminal of the sixth comparator 186 disposed at the downstream stage. The sixth comparator 186 determines the difference between the differential voltage Vk supplied to the inverting terminal and the target voltage Vm (for example, 450 mV) supplied to the non-inverting terminal. The voltage signal Vn, which represents the difference, is outputted from the output terminal. The voltage signal Vn is amplified with the predetermined gain by the third amplifier 188 disposed at the downstream stage, and the amplified voltage is supplied as the auxiliary pumping voltage Vp3 to the auxiliary pumping electrode 174 of the auxiliary pumping cell 170. In this embodiment, the inner pumping electrode 114 is connected to the GND line Lg to have the ground electric potential (0 V). Therefore, the voltage between the both electrodes 114, 174 of the auxiliary pumping cell 170 is consequently equivalent to the auxiliary pumping voltage Vp3 supplied from the third amplifier 188.

In this embodiment, the target oxygen concentration for the second chamber 112 is set to be lower than the target oxygen concentration for the first chamber 110, and hence a negative voltage is applied to the auxiliary pumping electrode 174. Accordingly, the oxygen in the second chamber 112 is pumped out to the first chamber 110 through the second solid electrolyte layer 102f.

That is, the auxiliary pumping cell 170 pumps out the oxygen contained in the measurement gas introduced into the second chamber 112 in an amount corresponding to the level of the auxiliary pumping voltage Vp3, to the first chamber 110. The series of operations are repeated, and thus the oxygen concentration in the second chamber 112 is subjected to feedback control to achieve the predetermined level.

As described above, in the gas sensor 100B according to the second embodiment, the oxygen to be pumped out by using the detecting pumping cell 134 and the auxiliary pumping cell 170 is pumped out toward the inner pumping electrode 114 connected to the GND line Lg of the DC power source 168. Therefore, when the oxygen is pumped out by the aid of the detecting pumping cell 134 and the auxiliary pumping cell 170, the negative voltage is applied to the detecting electrode 132 and the auxiliary pumping electrode 174 respectively.

Accordingly, the reference line (GND line Lg) of the power source for the pumping voltage Vp1 to be applied between the outer pumping electrode 116 and the inner pumping electrode 114 of the main pumping cell 118 can be used in common with those of the power source for the detecting voltage Vp2 to be applied between the detecting electrode 132 and the inner pumping electrode 114 of the detecting pumping cell 134 and the power source for the auxiliary pumping voltage Vp3 to be applied between the auxiliary pumping electrode 174 and the inner pumping electrode 114 of the auxiliary pumping cell 170.

As a result, it is unnecessary to prepare any separate DC power source which is insulated and independent (insulated type power source) in order to drive the detecting pumping cell 134 and the auxiliary pumping cell 170. Therefore, the detecting voltage Vp2 and the auxiliary pumping voltage Vp3 can be generated by using the non-insulated type power source which does not use any insulated type transformer. This consequently facilitates miniaturization of the control circuit system 150B of the gas sensor 100B and reduction of the weight thereof. Further, this facilitates miniaturization of the gas sensor 100B itself and reduction of the weight thereof.

Especially, in the gas sensor 100B according to the second embodiment, the electrode, which serves as the reference for the electric potential for constructing the main pumping cell 118, is used in common with the electrode which serves as the reference for the electric potential for constructing the detecting pumping cell 134 and the electrode which serves as the reference for the electric potential for constructing the auxiliary pumping cell 170, namely, all of the electrodes are commonly used as the inner pumping electrode 114. Therefore, when the inner pumping electrode 114 is connected to the GND line Lg as in this embodiment, it is possible to use the non-insulated type power source based on the use of semiconductor parts, as the power source for driving the detecting pumping cell 134 and the auxiliary pumping cell 170 respectively.

Accordingly, in the case of the gas sensor 100B according to the second embodiment, it is sufficient that the DC power source 168 or DC-DC converter is prepared as a number of individuals which is smaller than the number of the control circuits (the main pumping control circuit 152, the detecting pumping control circuit 154, and the auxiliary pumping control circuit 182). Especially, the electric power can be supplied from the power source to the respective control circuits (152, 154, 182) by preparing only one DC power source 168 or only one DC-DC converter connected to one DC power source 168.

Further, the gas sensor 100B according to the second embodiment may be constructed such that the inner pumping electrode 114 of the main pumping cell 118 is used in common with the measuring electrode 122 of the controlling oxygen partial pressure-measuring cell 126 (see FIG. 5), in the same manner as the modified embodiment 100Aa of the gas sensor 100A according to the first embodiment.

Next, explanation will be made with reference to FIG. 7 for a gas sensor 100C according to a third embodiment. Components or parts corresponding to those shown in FIG. 5 are designated by the same reference numerals, duplicate explanation of which will be omitted.

Figure 7:
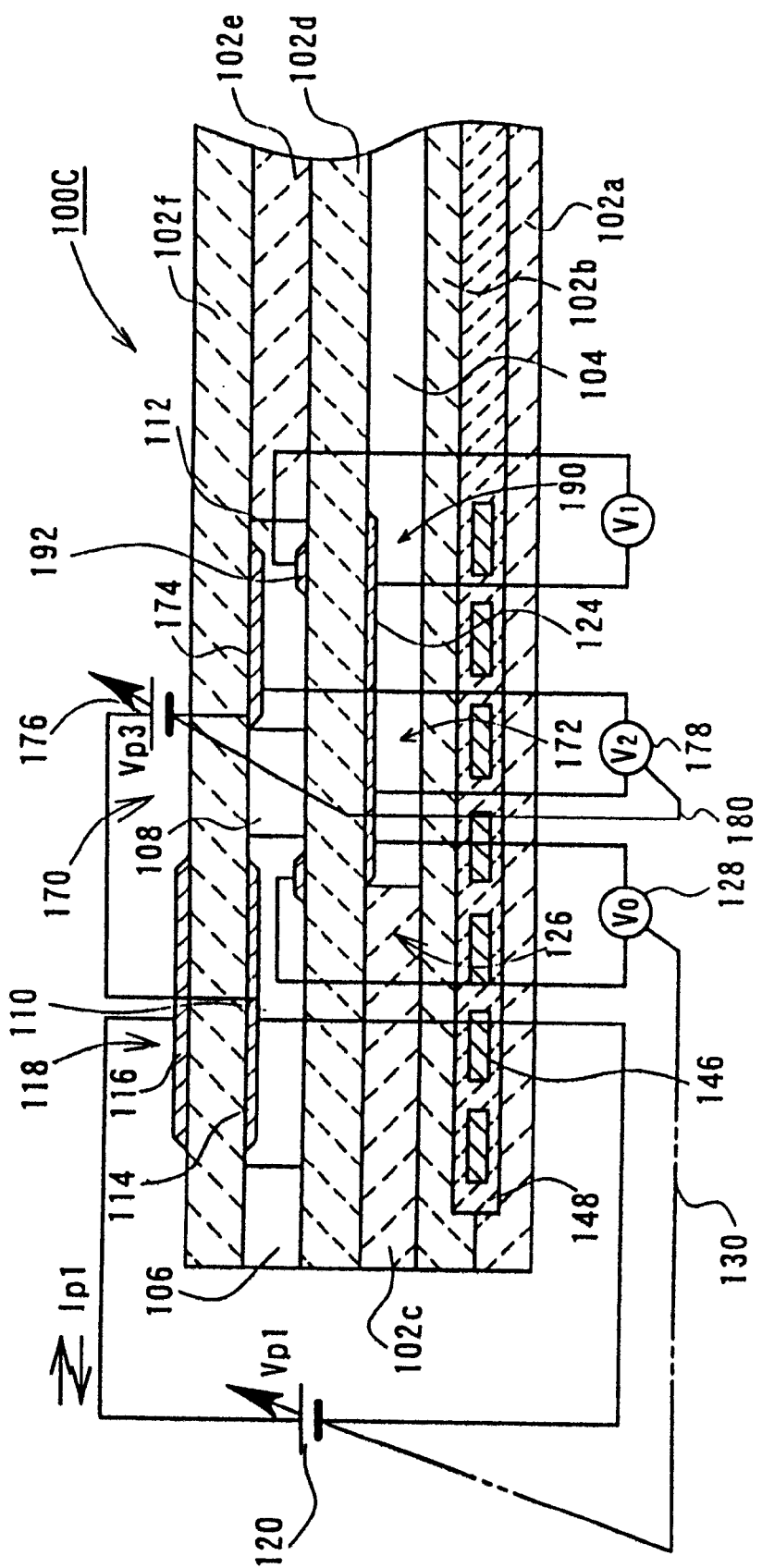
FIG. 7 shows a cross-sectional view illustrating a gas sensor according to a third embodiment.
Figure 8:
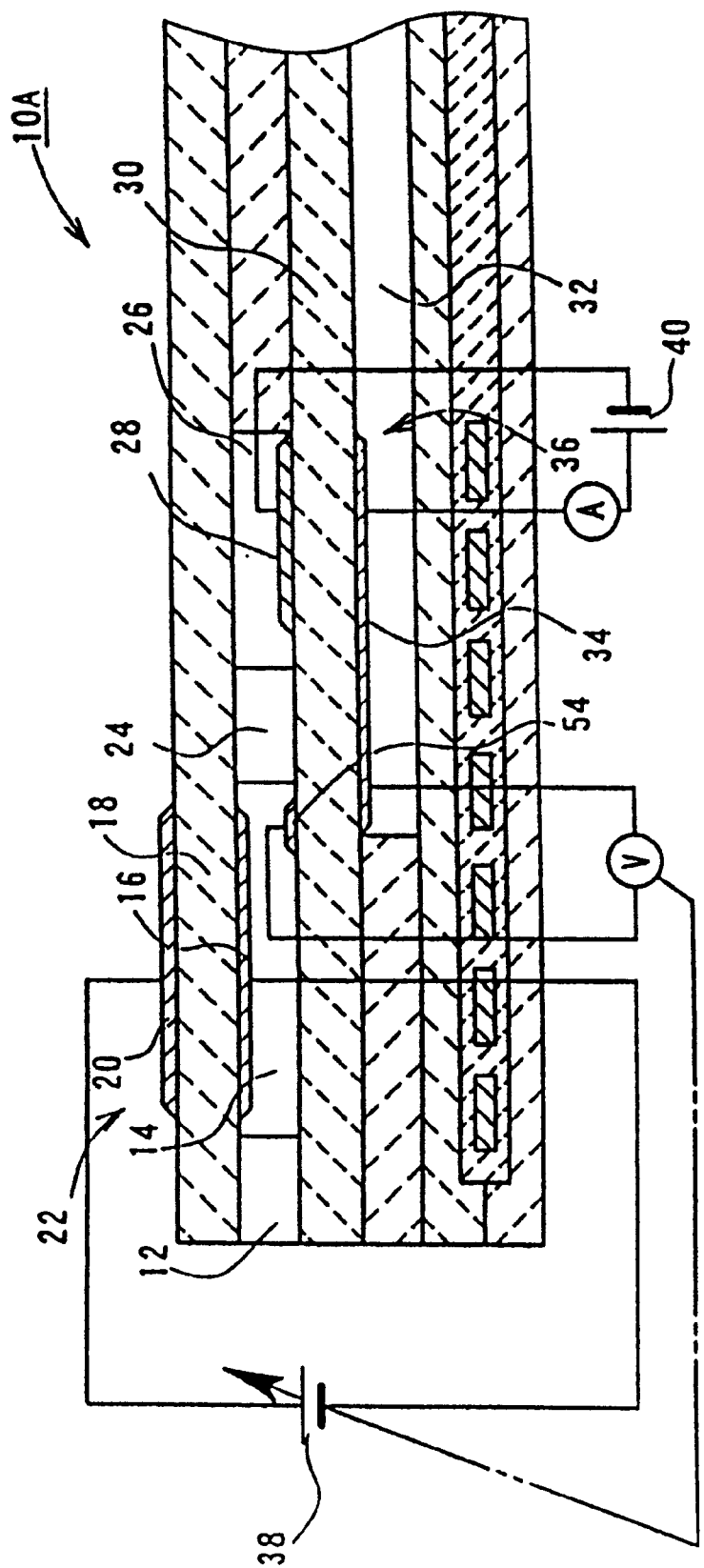
FIG. 8 shows a cross-sectional view illustrating a gas sensor concerning an illustrative conventional example.
Figure 9:
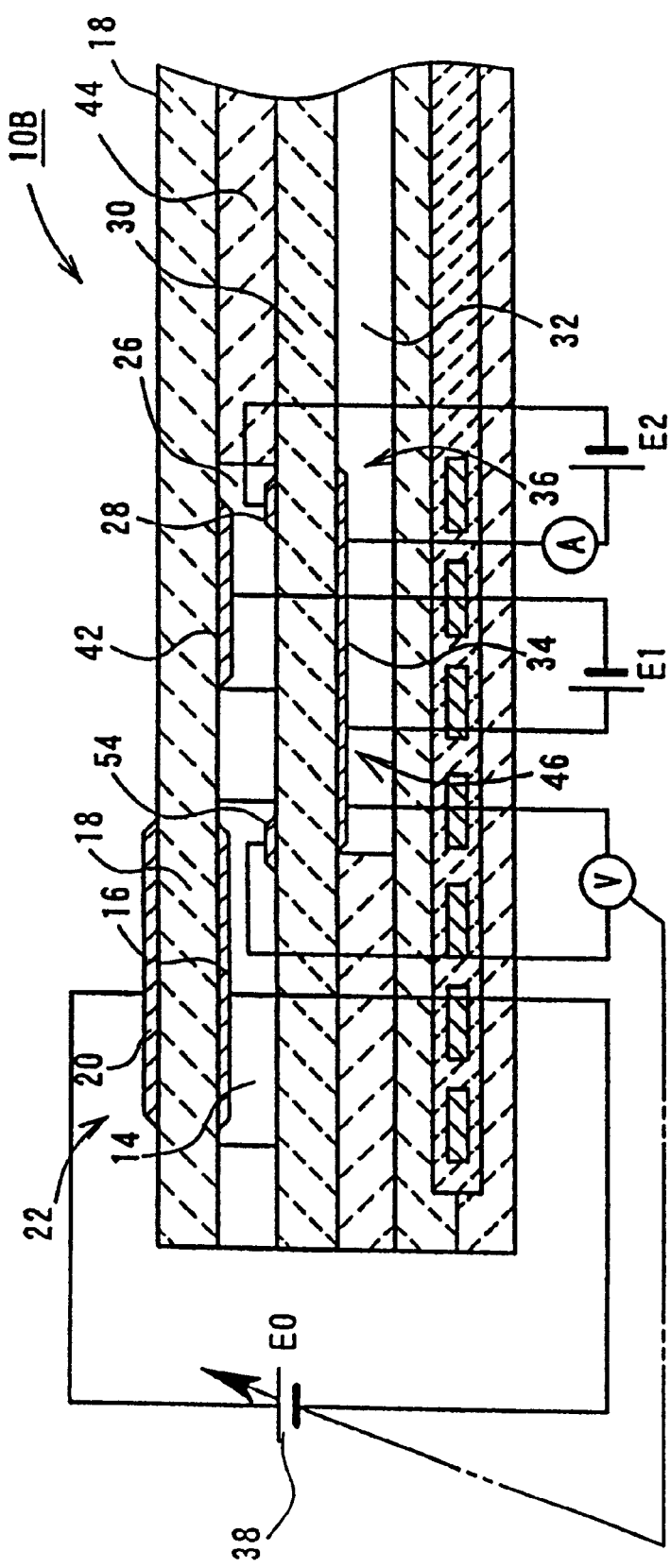
FIG. 9 shows a cross-sectional view illustrating a gas sensor concerning an illustrative suggested example.

As shown in FIG. 7, the gas sensor 100C according to the third embodiment is constructed in approximately the same manner as the gas sensor 100B according to the second embodiment described above. However, the former is different from the latter in that a detecting oxygen partial pressure-measuring cell 190 is used as the electrochemical sensor cell for detecting NOx, in place of the detecting pumping cell 134.

The detecting oxygen partial pressure-measuring cell 190 is constructed by a detecting electrode 192 formed on an upper surface portion for forming the second chamber 112, of the upper surface of the first solid electrolyte layer 102d, the reference electrode 124 formed on the lower surface of the first solid electrolyte layer 102d, and the first solid electrolyte layer 102d.

In this embodiment, an electromotive force (electromotive force of the oxygen concentration cell) V1, which corresponds to a difference in oxygen concentration between the atmosphere around the detecting electrode 192 and the atmosphere around the reference electrode 124, is generated between the detecting electrode 192 and the reference electrode 124 of the detecting oxygen partial pressure-measuring cell 190.

Therefore, the partial pressure of oxygen in the atmosphere around the detecting electrode 192, in other the partial pressure of oxygen defined by oxygen produced by reduction or decomposition of the measurement gas component (NOx) is detected as a voltage value V1 by measuring the electromotive force (voltage) V1 generated between the detecting electrode 192 and the reference electrode 124 by using a voltmeter 194.

The degree of change in the electromotive force V1 represents the NOx concentration. That is, the electromotive force V1, which is outputted from the detecting oxygen partial pressure-measuring cell 190 constructed by the detecting electrode 192, the reference electrode 124, and the first solid electrolyte layer 102$d$, represents the NOx concentration in the measurement gas.

Also in the gas sensor 100C according to the third embodiment, the oxygen to be pumped out by the auxiliary pumping cell 170 is pumped out toward the inner pumping electrode 114 connected to the GND line Lg of the DC power source 168. Therefore, the reference line (GND line Lg) of the power source for the pumping voltage Vp1 to be supplied to the main pumping cell 118 can be used in common with that of the power source for the auxiliary pumping voltage Vp3 to be supplied to the auxiliary pumping cell 170.

As a result, it is unnecessary to prepare any separate DC power source which is insulated and independent (insulated type power source) in order to drive the auxiliary pumping cell 170. Therefore, the auxiliary pumping voltage Vp3 can be generated by using the non-insulated type power source which does not use any insulated type transformer. This consequently facilitates miniaturization of the control circuit system of the gas sensor 100C and reduction of the weight thereof. Further, this facilitates miniaturization of the gas sensor 100C itself and reduction of the weight thereof.

By the way, in the case of the gas sensors 100A to 100C according to the first to third embodiments described above, the GND line Lg is connected to the inner pumping electrode 114 of the main pumping cell 118. However, the GND line Lg may be connected to the outer pumping electrode 116 of the main pumping cell 118. When the negative side lead wire of the heater 146 is connected to the outer pumping electrode 116, the line can be also used in common with GND of the heater 146. Thus, it is possible to simplify the wiring arrangement.

When the line is wired as described above, the oxygen in the first chamber 110 is pumped out to the external space by applying the negative voltage to the inner pumping electrode 114, while the oxygen in the external space is pumped into the first chamber 110 by applying the positive voltage to the inner pumping electrode 114.

The oxygen is pumped out from the second chamber 112 toward the outer pumping electrode 116 by the aid of the detecting pumping cell 134 (and the auxiliary pumping cell 170). The negative voltage is applied to the detecting electrode 132.

Usually, the insulative layer 148, which is formed to electrically insulate the heater 146 from the substrate layers 102$a$, 102$b$, has an insulation resistance of about several MΩ in a high temperature state. In this arrangement, when the GND line Lg is connected to the inner pumping electrode 114, for example, if a heater power source of 12 V is used, then a leak current of about several $\mu$A flows from the heater 146 to the inner pumping electrode 114. When the leak current flows through the first and second solid electrolyte layers 102$d$, 102$f$ which are oxygen ion conductors, the movement of oxygen takes place. The oxygen concentration in the first chamber 110 is affected by the magnitude of the leak current.

On the other hand, when the GND line Lg is connected to the outer pumping electrode 116, the leak current flows to the outer pumping electrode 116. In this arrangement, even when the movement of oxygen takes place, the oxygen concentration in the first chamber 110 is not affected thereby.

The inner pumping electrode 114 is arranged in the first chamber 110. Therefore, when the oxygen in the second chamber 112 is pumped out toward the inner pumping electrode 114 by the aid of the detecting pumping cell 134 and the auxiliary pumping cell 170, it is necessary that the oxygen corresponding to the amount pumped out as described above should be pumped out again to the external space by using the main pumping cell 118.

On the contrary, when the oxygen in the second chamber 112 is pumped out toward the outer pumping electrode 116, an advantage is obtained in that no pumping operation is required by using the main pumping cell 118 again when the measurement gas in the external space has an $O_2$-rich atmosphere.

The DC power source 168 may be arranged as follows. That is, voltages of 0 V, +5 V, and −5 V are allowed to appear through the GND line Lg, the positive (+) side power source line L1, and the negative (−) side power source line L2 led from the DC power source 168. Alternatively, a battery voltage (0 to 12 V) may be divided at the middle point to make use of 6 V (ground voltage assumed for signals), 12 V (positive (+) power source voltage), and 0 V (negative (−) power source voltage).

In the gas sensors 100A to 100C according to the first to third embodiments described above (including the modified embodiments), NOx is the objective as the measurement gas component. However, the present invention is also effectively applicable to the measurement of bound oxygen-containing gas components other than NOx, for example, $H_2O$ and $CO_2$, which would be otherwise affected by the oxygen existing in the measurement gas.

It is a matter of course that the gas sensor and the method for controlling the gas sensor according to this invention is not limited to the embodiments described above, which may be constructed in various forms without deviating from the gist or essential characteristics of this invention.

What is claimed is:

1. A gas sensor comprising:
   a main pumping means for pumping-processing oxygen contained in a measurement gas introduced from external space into a processing space formed and comparted by an external solid electrolyte contacting with said external space so that a partial pressure of oxygen in said processing space is controlled to have a predetermined value; and
   a detecting pumping means for decomposing a predetermined gas component as a measurement objective contained in said measurement gas after being pumping-processed by said main pumping means by the aid of a catalytic action and/or electrolysis, and pumping-processing oxygen produced by said decomposition, wherein:
   said predetermined gas component contained in said measurement gas is measured on the basis of a pumping current which is allowed to flow through said detecting pumping means in accordance with said pumping process effected by said detecting pumping means; and
   said detecting pumping means having means for pumping out said oxygen produced by said decomposition toward an electrode of said main pumping means which is fixed to have a base electric potential.

2. The gas sensor according to claim 1, wherein:

said main pumping means comprises said external solid electrolyte contacting with said external space, and an inner main pumping electrode and an outer main pumping electrode on inner and outer surfaces of said external solid electrolyte;

said detecting pumping means comprises an internal solid electrolyte, and an inner detecting pumping electrode in contact with said internal solid electrolyte and an outer detecting pumping electrode in contact with said external solid electrolyte;

any one of said pumping electrodes of said main pumping means is used in common with said outer detecting pumping electrode of said detecting pumping means; and any one of said pumping electrodes is fixed to have said base electric potential.

3. The gas sensor according to claim 2, further comprising:

a main pumping concentration-measuring means for generating an electromotive force corresponding to a difference between an amount of oxygen contained in a reference gas and an amount of oxygen contained in said measurement gas during said pumping process effected by said main pumping means; and a main pumping control means for controlling said pumping process effected by said main pumping means by adjusting a level of a control voltage applied between said inner main pumping electrode and said outer main pumping electrode of said main pumping means, on the basis of said electromotive force.

4. The gas sensor according to claim 2, further comprising:

a detecting concentration-measuring means for generating an electromotive force corresponding to a difference between an amount of oxygen contained in a reference gas and an amount of oxygen produced during said decomposition of said predetermined gas component contained in said measurement gas after being pumping-processed by said main pumping means; and a detecting pumping control means for controlling said pumping process effected by said detecting pumping means by adjusting a level of a detecting voltage applied between said inner detecting pumping electrode and said outer detecting pumping electrode of said detecting pumping means, on the basis of said electromotive force.

5. The gas sensor according to claim 1, further comprising an auxiliary pumping means including said external solid electrolyte and an inner auxiliary pumping electrode and an outer auxiliary pumping electrode in contact with said external solid electrolyte, for pumping out oxygen contained in said measurement gas after being pumping-processed by said main pumping means toward said outer auxiliary pumping electrode.

6. A gas sensor comprising:

a main pumping means for pumping-processing oxygen contained in a measurement gas introduced from external space into a processing space formed and comparted by an external solid electrolyte contacting with said external space so that a partial pressure of oxygen in said processing space is controlled to have a predetermined value; and a concentration-detecting means for decomposing a predetermined gas component as a measurement objective contained in said measurement gas after being pumping-processed by said main pumping means by the aid of a catalytic action, and generating an electromotive force corresponding to a difference between an amount of oxygen produced by said decomposition and an amount of oxygen contained in a reference gas, wherein:

said predetermined gas component contained in said measurement gas is measured on the basis of said electromotive force detected by said concentration-detecting means;

said gas sensor further comprising an auxiliary pumping means for pumping out additional oxygen contained in said measurement gas after being pumping-processed by said main pumping means and before said predetermined gas component is decomposed to produce oxygen toward an electrode of said main pumping means which is fixed to have a base electric potential.

7. The gas sensor according to claim 6, wherein:

said main pumping means comprises said external solid electrolyte contacting with said external space, and an inner main pumping electrode and an outer main pumping electrode on inner and outer surfaces of said external solid electrolyte;

said auxiliary pumping means comprises said external solid electrolyte, and an inner auxiliary pumping electrode and an outer auxiliary pumping electrode in contact with said external solid electrolyte;

any one of said pumping electrodes of said main pumping means is used in common with said outer auxiliary pumping electrode of said auxiliary pumping means; and any one of said pumping electrodes is fixed to have said base electric potential.

8. The gas sensor according to claim 7, further comprising:

a main pumping concentration-measuring means for generating an electromotive force corresponding to a difference between said amount of oxygen contained in said reference gas and an amount of oxygen contained in said measurement gas during said pumping process effected by said main pumping means; and a main pumping control means for controlling said pumping process effected by said main pumping means by adjusting a level of a control voltage applied between said inner main pumping electrode and said outer main pumping electrode of said main pumping means, on the basis of said electromotive force.

9. The gas sensor according to claim 7, further comprising:

an auxiliary concentration-measuring means for generating an electromotive force corresponding to a difference between said amount of oxygen contained in said reference gas and an amount of oxygen contained in said measurement gas after being pumping-processed by said main pumping means; and an auxiliary pumping control means for controlling said pumping process effected by said auxiliary pumping means by adjusting a level of an auxiliary pumping voltage applied between said inner auxiliary pumping electrode and said outer auxiliary pumping electrode of said auxiliary pumping means, on the basis of said electromotive force.

10. The gas sensor according to claim 7, wherein said outer auxiliary pumping electrode of said auxiliary pumping means is used in common with said electrode of said main pumping means which is fixed to have said base electric potential.

11. A method for controlling a gas sensor comprising:

pumping-processing oxygen contained in a measurement gas introduced from external space into a processing space formed and comparted by a solid electrolyte contacting with said external space by using a main pumping means so that a partial pressure of oxygen in said processing space is controlled to have a predetermined value;

decomposing a predetermined gas component as a measurement objective contained in said measurement gas after being pumping-processed by said main pumping means by the aid of a catalytic action and/or electrolysis by using a detecting pumping means to pumping-process oxygen produced during said decomposition; and measuring said predetermined gas component contained in said measurement gas on the basis of a pumping current flowing through said detecting pumping means in accordance with said pumping process performed by said detecting pumping means, wherein:

said oxygen produced during said decomposition to be pumped out by said detecting pumping means is pumped out toward an electrode of said main pumping means which is fixed to have a base electric potential.

12. The method for controlling the gas sensor according to claim 11, further comprising:

measuring an electromotive force corresponding to a difference between an amount of oxygen contained in a reference gas and an amount of said oxygen produced during said decomposition of said predetermined gas component contained in said measurement gas after being pumping-processed by said main pumping means, by using a detecting concentration-measuring means; and adjusting said pumping process performed by said detecting pumping means on the basis of said electromotive force measured by said detecting concentration-measuring means.

13. The method for controlling the gas sensor according to claim 11, further comprising pumping out said oxygen contained in said measurement gas after being pumping-processed by said main pumping means toward said processing space for said main pumping means, by using an auxiliary pumping means.

14. The method for controlling the gas sensor according to claim 11, further comprising:

measuring an electromotive force corresponding to a difference between an amount of oxygen contained in a reference gas and an amount of oxygen contained in said measurement gas after being pumping processed by said main pumping means, by using an auxiliary concentration-measuring means; and adjusting a pumping process performed by an auxiliary pumping means on the basis of said electromotive force measured by said auxiliary concentration-measuring means.

15. The method for controlling the gas sensor according to claim 11, further comprising:

measuring an electromotive force corresponding to a difference between an amount of oxygen contained in a reference gas and an amount of oxygen contained in said measurement gas during said pumping process performed by said main pumping means, by using a main pumping concentration-measuring means; and adjusting said pumping process performed by said main pumping means on the basis of said electromotive force measured by said main pumping concentration-measuring means.

16. A method for controlling a gas sensor comprising:

pumping-processing oxygen contained in a measurement gas introduced from external space into a processing space formed and comparted by a solid electrolyte contacting with said external space by using a main pumping means so that a partial pressure of oxygen in said processing space is controlled to have a predetermined value;

decomposing a predetermined gas component as a measurement objective contained in said measurement gas after being pumping-processed by said main pumping means by the aid of a catalytic action by using a concentration-detecting means to detect an electromotive force generated corresponding to a difference between an amount of oxygen contained in a reference gas and an amount of oxygen produced during said decomposition; and measuring said predetermined gas component contained in said measurement gas on the basis of said electromotive force detected by said concentration-detecting means, wherein:

additional oxygen contained in said measurement gas after being pumping-processed by said main pumping means is pumped out by using an auxiliary pumping means toward an electrode of said main pumping means which is fixed to have a base electric potential before said predetermined gas component is decomposed to produce oxygen.

17. The method for controlling the gas sensor according to claim 16, further comprising:

measuring an electromotive force corresponding to a difference between said amount of oxygen contained in said reference gas and an amount of oxygen contained in said measurement gas after being pumping processed by said main pumping means, by using an auxiliary concentration-measuring means; and adjusting said pumping process performed by said auxiliary pumping means on the basis of said electromotive force measured by said auxiliary concentration-measuring means.

18. The method for controlling the gas sensor according to claim 16, further comprising:

measuring an electromotive force corresponding to a difference between said amount of oxygen contained in said reference gas and an amount of oxygen contained in said measurement gas during said pumping process performed by said main pumping means, by using a main pumping concentration-measuring means; and adjusting said pumping process performed by said main pumping means on the basis of said electromotive force measured by said main pumping concentration-measuring means.

* * * * *